US010712837B1

(12) United States Patent
Douglas et al.

(10) Patent No.: US 10,712,837 B1
(45) Date of Patent: Jul. 14, 2020

(54) USING GEO-REGISTERED TOOLS TO MANIPULATE THREE-DIMENSIONAL MEDICAL IMAGES

(71) Applicants: David Douglas, Winter Park, FL (US); Robert Douglas, Winter Park, FL (US); Kathleen Douglas, Winter Park, FL (US)

(72) Inventors: David Douglas, Winter Park, FL (US); Robert Douglas, Winter Park, FL (US); Kathleen Douglas, Winter Park, FL (US)

( * ) Notice: Subject to any disclaimer, the term of this patent is extended or adjusted under 35 U.S.C. 154(b) by 0 days.

(21) Appl. No.: 16/524,275

(22) Filed: Jul. 29, 2019

Related U.S. Application Data

(60) Provisional application No. 62/711,658, filed on Jul. 30, 2018.

(51) Int. Cl.
*G06T 15/00* (2011.01)
*G06F 3/0346* (2013.01)
*G06F 3/0354* (2013.01)
*G06F 3/0481* (2013.01)
*G06F 3/0484* (2013.01)
*A61B 5/06* (2006.01)
*G06T 19/20* (2011.01)

(52) U.S. Cl.
CPC ............ *G06F 3/0346* (2013.01); *A61B 5/067* (2013.01); *G06F 3/03545* (2013.01); *G06F 3/04815* (2013.01); *G06F 3/04845* (2013.01); *G06T 19/20* (2013.01); *G06T 2210/41* (2013.01); *G06T 2219/004* (2013.01); *G06T 2219/2016* (2013.01)

(58) Field of Classification Search
USPC ......................................................... 345/419
See application file for complete search history.

(56) References Cited

U.S. PATENT DOCUMENTS

| | | | | |
|---|---|---|---|---|
| 2013/0286053 | A1* | 10/2013 | Fleck | G09G 3/3208 345/690 |
| 2015/0205126 | A1* | 7/2015 | Schowengerdt | G06F 3/011 345/633 |
| 2016/0027218 | A1* | 1/2016 | Salter | G02B 27/0172 345/633 |
| 2018/0116728 | A1* | 5/2018 | Lang | A61B 34/10 |
| 2018/0168740 | A1* | 6/2018 | Ryan | A61B 1/317 |
| 2018/0325601 | A1* | 11/2018 | Mak | G06T 15/00 |

* cited by examiner

Primary Examiner — Gordon G Liu
(74) Attorney, Agent, or Firm — Anderson Gorecki LLP

(57) ABSTRACT

A virtual object that represents a tangible object is displayed in a three-dimensional image. Responsive to a first input which may be movement of the tangible object, the virtual object moves within the three-dimensional image. Alteration of how the three-dimensional image is displayed occurs responsive to a second input. For example, virtual medical tools can be controlled by manipulating tangible tools to perform procedures and tasks virtually. Eye tracking can be used to generate variable angular resolution in the field of view in a head display unit with which the three-dimensional image is displayed. Digital objects may be used to cause the viewer's eyes move from feature to feature in a saccades fashion or a smooth tracking fashion.

44 Claims, 20 Drawing Sheets

MASTER CONTROL PANEL SITS ON RADIOLOGIST'S DESK WITH
REGISTRATION POINT(S)

| Tangible Item | Key Design Element | Key Functions |
|---|---|---|
| Control platform | Ability to register objects | Master control system for segmentation, filtering and rendering, move volumes, interactive 3D cursors, advanced function control (e.g., inserting/stretching voxels, etc.) |

GEO-REGISTERED HEAD DISPLAY UNIT

| Tangible Item | Key Design Element | Key Functions |
|---|---|---|
| Head Display Unit | Position tracking (XYZ), orientation tracking (RPY) | Provides stereoscopic vision, optimization of pixels/degree FOV based on convergence, looking direction and item of interest |

GEO-REGISTERED FOCAL POINT PEN

| Tangible Item | Key Design Element | Key Functions |
|---|---|---|
| Focal point pen | Position tracking (XYZ), orientation tracking (RPY) | Provides enhanced viewing (e.g., guides focal point convergence, smooth tracking). Provides ability to select tissues of interest (e.g., select blood vessels to be separated). Provides annotations. |

GEO-REGISTERED HAND-HELD PLATFORM

| Tangible Item | Key Design Element | Key Functions |
|---|---|---|
| Hand held platform | Position tracking (XYZ), orientation tracking (RPY) | Provides ability to fix a virtual structure to the tangible real-world object for rotate/translate whole or sub-volume in palm of hand (e.g., holding heart in one's hand) |

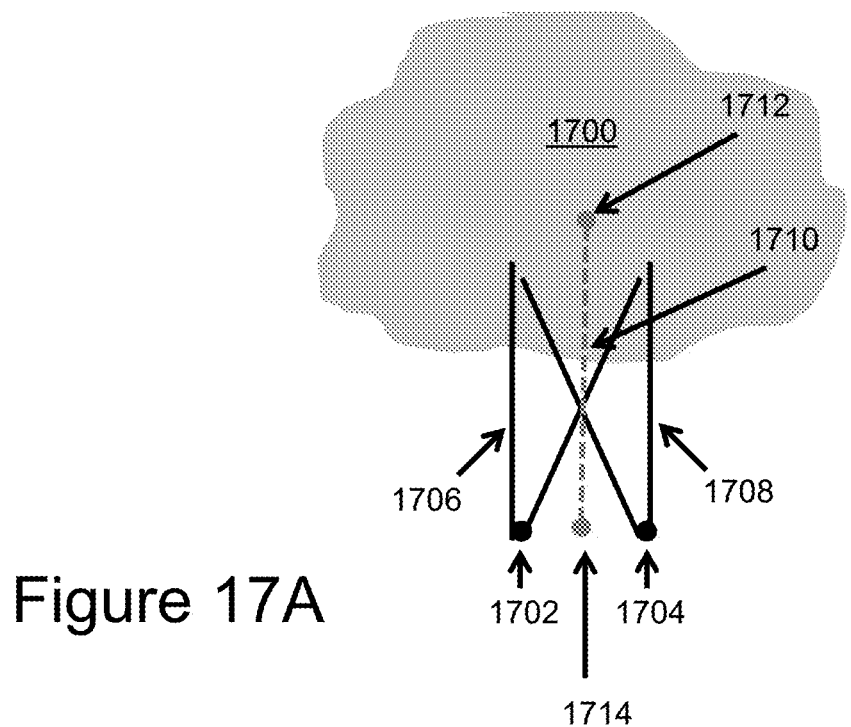
Figure 17A
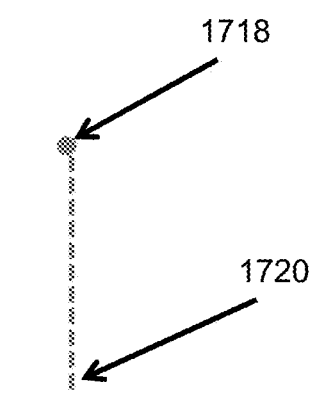
Figure 17B
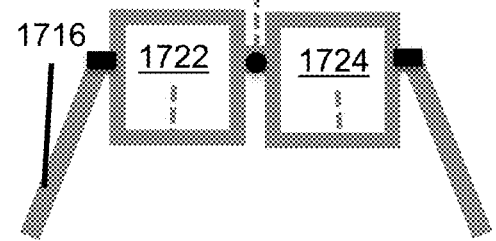

USING GEO-REGISTERED TOOLS TO MANIPULATE THREE-DIMENSIONAL MEDICAL IMAGES

TECHNICAL FIELD

Aspects of this disclosure are generally related to presentation of volumetric medical images.

BACKGROUND

A recent advance in the field of diagnostic radiology is disclosed in U.S. Pat. No. 8,384,771 titled METHOD AND APPARATUS FOR THREE DIMENSIONAL VIEWING OF IMAGES, which is incorporated by reference. Three-dimensional medical images are presented via an augmented reality, virtual reality or mixed reality headset. Perception of depth is enabled by generating different images for each eye.

SUMMARY

All examples, aspects and features mentioned in this document can be combined in any technically possible way.

In some implementations, a user controller interface for presentation of 3D medical images comprises a joystick and functional buttons. Functionality provided by the buttons for review digitally may include, but is not limited to: a) changing orientation (roll, pitch, yaw) of a 3D cursor; b) zooming viewpoint toward and away from the 3D cursor; c) invoking convergence; d) raising and lowering where the 3D cursor is displayed on the headset; e) changing the size, shape, and color of the 3D cursor; e) invoking filtering, segmentation, sequencing, statistical, and reporting operations; f) invoking pointer and movement control thereof; g) annotating one or more 3D cursors within the volume of interest; and h) invoking icon options.

Some implementations include tangible equipment items with position and orientation tracking, possibly including, but not limited to, one or more of: a desk registration component equipped with registration points; a focal point pen with registration points, position and orientation tracking; a platform with registration points, position and orientation tracking; a multifunction tool with registration points, position and orientation tracking; a head display unit (e.g., augmented reality, virtual reality or mixed reality) equipped with registration points, position and orientation tracking and innovative convergence capabilities; a cutting device equipped with registration points, position and orientation tracking; and, a catheter device, which could also have the option for tracking. The items may enable performance of virtual tasks possibly including: control of a digital pointer; control of a 3D cursor; interaction with virtual tissues through the hand-held tools, such as pulling virtual tissues together or spreading them apart; step-through sequencing; and annotation. Implementation of these virtual tasks may include filtering, segmentation, voxel manipulations and coordinated multi-voxel shifts, as disclosed in U.S. patent application Ser. No. 15/904,092 titled PROCESSING 3D MEDICAL IMAGES TO ENHANCE VISUALIZATION and U.S. patent application Ser. No. 16/195,251 titled INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, both of which are incorporated by reference.

Some implementations comprise a display icon that illustrates a human body facing in a direction specified by the medical person viewing the medical images. The icon may comprise one or more of: a) a depiction of the current viewing point properly located relative to the human body icon; b) a depiction of the outline of volume of interest being examined within the human body icon; and c) the location of the 3D cursor. Further, during the course of the examination wherein the 3D cursor and contents would have been extracted-manipulated to some degree (e.g., voxel changed from initial orientation rolling, pitching and/or yaw commands to a new orientation), the medical personnel could specify a new icon that depicts to 3D cursor along with both initial viewing point and current viewing point properly located with, for example, an arrow originating at the initial viewing point and terminating at the current viewing point.

Some implementations comprise one or more of: a geo-registration coordinate system; geo-registered volumetric medical images; head display unit with tracking and orientation; focal point pen with tracking and orientation; a virtual pedestal/platform with tracking and orientation; a knife with tracking and orientation, a 3D cursor with tracking and orientation, and a desk registration component. Using the technique described in U.S. patent application Ser. No. 15/949,202, the patient's medical images would be associated with a volumetric coordinate system. A focal point pen could be registered with the volumetric coordinate system. Using a geo-registration point on the head display unit, the head display unit could be geo-registered with the volumetric coordinate system. Further, using a geo-registration point on a knife unit, the knife unit could be geo-registered with the volumetric coordinate system. A virtual pedestal/platform could be registered with the volumetric coordinate system. Further, a 3D cursor (e.g. as described in U.S. Pat. No. 9,980,691) could be geo-registered and moveable via commands entered by the medical personnel using a hand control unit. A copy of the 3D cursor contents could be made and sent to other locations for examination (e.g., place on pedestal/platform). Thus, geo-registration of various components with the patient's medical images is enabled in an overall volumetric coordinate system.

Some implementations include a virtual environment comprising at least one of: a geo-registration coordinate system; a head display unit with tracking and orientation; a focal point pen with tracking and orientation; a multifunction tool tracking and orientation; a virtual pedestal/platform with tracking and orientation; and a desk registration component. The patient's medical images would be associated with or include a volumetric coordinate system as described above. The focal point pen, head display unit, desk registration component, and virtual pedestal/platform could each be independently registered with the medical image volumetric coordinate system.

Some implementations include head movement and head orientation tracking. Orientation and movement may be measured by an inertial measurement system within the head display unit. Further, the head display unit would have a registration point which would, when touching the geo-registration component, in conjunction with geo-processing software, enable geo-registration of the head display unit within the medical image volumetric coordinate system. Movements of the head display unit in location (i.e., X, Y, and Z coordinates) and orientation (i.e., roll, pitch, and yaw) would be transmitted to a computer via a transmitter within the head display unit. The computer would compute how these head movements would affect the 3D volume being displayed and create an adjusted volume for display. The adjusted volume would be transmitted by the computer and received by the receiver element in the head set and subsequently shown on the head display unit eye pieces.

The geo-registered focal point pen may be a geo-registered physical object to be held in the hand of medical personnel. The focal point pen unit would have a registration point which would, when touching the geo-registration component, in conjunction with geo-processing software, enable geo-registration of the focal point pen unit within the overall system containing the volumetric medical images and other system components. These movements of the focal point pen in location (i.e., X, Y, and Z coordinates) and orientation (i.e., roll, pitch, and yaw) would be obtained by an inertial measurement unit within the pen and transmitted to the computer via a transmitter also within the pen. Functionality of the focal point pen could comprise one or more of the following: a) moving the focal point pen within the 3D image set so as to follow arteries/veins within a complex vascular structure; b) touching a point within the 3D image set with the tip of the pen for annotation and/or cross reference the a particular 2D image slice; c) writing notes, drawing symbols (e.g., encircle tissue of concern; draw arrows) and; d) color coding could be invoked by medical personnel.

Some implementations include a method of using the focal point pen comprising one or more of the following steps: a) moving the focal point pen within the 3D image set so as to follow arteries/veins within a complex vascular structure; b) touching a point within the 3D image set with the tip of the pen for annotation and/or cross reference the a particular 2D image slice; c) writing notes, drawing symbols (e.g., encircle tissue of concern; draw arrows); d) selecting tissue type to assign physical property (e.g., assigning bone a rigid physical property); and e) selecting tissue types for where to add voxels so to separate tissues apart to better visualize complex anatomical structures (e.g., separating the tangle of blood vessels in a cerebral arteriovenous malformation).

Some implementations include a method for assigning physical properties to tissue types, comprising one or more of the following steps: a) assigning a stretchable property to voxels of certain tissue types (e.g., muscle, tendon, etc.); b) assigning points of fixation (e.g., tendon or ligament insertion site into the bone); c) assigning a rigid property to voxels of certain tissue types (e.g. bone); d) assigning a rigid, but mobile property to tissue type (e.g., shoulder's ball and socket joint); and e) assigning non-fixed, fluid property to certain tissue types (e.g., blood inside blood vessel).

Some implementations include calibration to ensure component accuracy. To verify the accuracy of the geo-registered components, it may be desirable to perform a check using calibration points. The first step is to have the medical personnel arbitrarily place 6 or more calibration points into the geo-registration coordinate system. The next step is for the medical personnel to touch each of the points with the system components and check that the coordinates shown by the component match those of the calibration points.

The geo-registered pedestal/platform may be a geo-registered physical object to be held in the hand of medical personnel. The pedestal/platform unit may have a registration point which would, when touching the geo-registration component, in conjunction with geo-processing software, enable geo-registration of the pedestal/platform unit within the overall system containing the volumetric medical images and other system components. These movements of the pedestal/platform in location (i.e., X, Y, and Z coordinates) and orientation (i.e., roll, pitch, and yaw) would be obtained by an inertial measurement unit within the pedestal/platform and transmitted to the computer via the transmitter also within the pedestal/platform unit. Functionality of the pedestal/platform may include moving the pedestal/platform to a volume of interest within the 3D medical image (e.g., volume contained within the 3D cursor) by hand movements of the pedestal/platform and then the medical person viewing the medical images issues command to affix the volume of interest to the pedestal/platform. The medical person viewing the medical images by hand control of the pedestal/platform could rotate, tilt the pedestal/platform and move the pedestal/platform closer/further for examination. Additionally, this examination process could be accompanied by head movements by medical person viewing the medical images so as to obtain a better perspective of any tissue of potential concern.

Some implementations include moving the pedestal/platform to a volume of interest within the 3D medical image (e.g., volume contained within the 3D cursor) by hand movements of the pedestal/platform and then the medical person viewing the medical images issues a command to affix the volume of interest to the pedestal/platform. The medical person viewing the medical images by hand control of the pedestal/platform could rotate, tilt, or translate the pedestal/platform for examination. Further, this examination process could be accompanied by simultaneous head movements by medical person viewing the medical images so as to obtain a better perspective of any tissue of potential concern.

Some implementations include a geo-registered 3D virtual cursor. The 3D virtual cursor might have some of the features described in U.S. Pat. No. 9,980,691 and U.S. patent application Ser. No. 15/878,463, both of which are incorporated by reference. The contents within the 3D virtual cursor could be copied and moved within the overall geo-registration system to a different geo-registered position (e.g., the pedestal/platform). The 3D virtual cursor contents could be affixed to the pedestal/platform and moved in concert with the pedestal/platform movements. The 3D virtual cursor movements and selection of contents would be at the at the command of medical personnel through the control unit to the computer.

Some implementations include an ablation method. The ablation technique could be used in conjunction with a 3D digital mass, transported by the 3D cursor as described above and affixed to geo-located pedestal/platform. The first step may be determining the outer 'shell' of an organ of interest to the medical person viewing the medical images (e.g., using segmentation techniques described in U.S. patent application Ser. No. 15/904,092, which is incorporated by reference); sequentially eliminating one voxel deep layers from the outer surface at the direction of the medical person viewing the medical images; alternatively or additionally, selecting one layer in the X, Y, Z coordinate system (e.g., select the X-Y layer with the highest Z coordinate and eliminating that layer at the direction of the medical person viewing the medical images.

The geo-registered 'knife' may be a geo-registered physical object to be held in the hand of medical personnel. The knife unit may have a registration point which would, when touching the geo-registration component, in conjunction with geo-processing software, enable geo-registration of the knife unit within the overall system containing the volumetric medical images and other system components. These movements of the knife in location (i.e., X, Y, and Z coordinates) and orientation (i.e., roll, pitch, and yaw) would be obtained by an inertial measurement unit within the knife and transmitted to the computer via a transmitter also within the knife. The geo-registered knife could be used by medical personnel to 'carve away tissue' from a geo-registered 3D digital mass. The geo-registered knife could be used in conjunction with a 3D digital mass mounted on the virtual pedestal/platform and/or within the 3D cursor. The geo-registered knife would be geo-registered within the geo-registration system and could be used by the medical person viewing the medical images to pick up the geo-registered knife and move it to the 3D digital mass of current interest, then pass the geo-registered knife through the 3D geo-registered digital mass. Tissue which is external to the surface created by the geo-registered knife when it passed through the 3D geo-registered digital mass (the side of the geo-registered knife pre-selected by the medical person viewing the medical images for 3D tissue extraction form the 3D digital mass) would be virtually removed. The knife may include an exact registration point (e.g., tip of geo-registered knife), additional geo-registration points to indicate the cutting surface of the knife and an internal measurement unit to provide changes in the X, Y, Z coordinate system and also roll, pitch and yaw of the knife.

Some implementations include a multi-function tool that can be used for grabbing a tissue type within the 3D medical volume. Steps may include moving the multi-function tool to a volume of interest within the 3D medical image (e.g., volume contained within the 3D cursor) by hand movements of the multi-function tool and then the medical person viewing the medical images issuing a command to affix a portion of the tissue subtype to the multi-function tool. The medical person viewing the medical images by hand control of the multi-function tool could affix the multi-function tool to a tissue and move the selected tissue (i.e. exert force on the tissue structure to translate, rotate, pull it) such that the selected tissue moves in accordance with its assigned physical property and the assigned physical properties of the nearby adjacent structures.

In some implementations the multi-function tool may be used for cutting a tissue type within the 3D medical volume. Steps may include moving the MFT to a volume of interest within the 3D medical image (e.g., volume contained within the 3D cursor) by hand movements of the MFT and then the medical person viewing the medical images issuing a command to cut a portion of the tissue subtype using the multi-function tool. The medical person viewing the medical images by hand control of the multi-function tool could affix the multi-function tool to a tissue and move the selected tissue (i.e. exert force on the tissue structure to translate, rotate, pull it) such that the selected tissue moves in accordance with its assigned physical property and the assigned physical properties of the nearby adjacent structures.

Some implementations include utilizing the multi-function tool for fixing a tissue type within the 3D medical volume. Steps may include moving the multi-function tool to a volume of interest within the 3D medical image (e.g., volume contained within the 3D cursor) by hand movements of the multi-function tool and then the medical person viewing the medical images issuing a command to attach one tissue subtype to another tissue subtype using the multi-function tool.

Some implementations include a 3D geo-registered catheter. The 3D geo-registered catheter may be used in conjunction geo-registration of medical images as described in U.S. patent application Ser. No. 15/949,202 or U.S. Pat. No. 9,301,809, both of which are incorporated by reference. The radiologist/interventionist could switch back and forth between the geo-registered 3D system using the 3D head mounted display and standard displays currently available in interventional operations. This permits utilization of distance markers and 3D screen captures generated during pre-operative planning. Further, alerts could be given in near real time as critical junctions were being approached.

In some implementations the geo-registered catheter is used in conjunction with a 3D digital image of the vascular structure within the patient. The catheter could continuously compute the total distance travelled which could be displayed, and time-tagged and recorded for later review. The geo-registered catheter could be used during pre-operative planning of an interventional procedure including, but not limited to, treatment of a middle cerebral artery aneurysm. Steps may include: inserting the geo-registered catheter into the 3D digital vascular structure at a pre-determined point such as the groin of the patient into the common femoral artery, then the external iliac artery, then the common iliac artery, then the abdominal aorta, then the thoracic aorta, then the brachiocephalic artery, then the common carotid artery, then the internal carotid artery then the middle cerebral artery, and finally into the aneurysm. Augmented reality distance markers could be added to each intersection. Each succeeding element of the catheter goes to the location and orientation of the immediately proceeding (or trailing) element as the radiologist pushes (or pulls) on the catheter.

The user controller interface may enable medical personnel reviewing 3D medical images to review inputs provided via geo-registered tools. Functionality for review virtually may include, but is not limited to, the following when interfacing with the 3D cursor: a) changing the orientation of the 3D cursor roll, pitch and yaw, such as moving the hand-held geo-registered platform temporarily attached to the 3D cursor of interest; b) zooming the medical person viewpoint in toward the 3D cursor and out away from the cursor, such as moving the hand-held platform temporarily attached to the 3D cursor closer to the left and the right eye viewing perspectives or a leaning forward action to move the persons eyes closer to their hand; c) invoking convergence, such as moving a focal point pen acting as a convergence point for objects in the volumetric medical imaging database; d) raising and lowering the 3D cursor as to where it is displayed on the headset, such as raising or lowering the radiologist's chair and keeping the radiologist's desk, master control platform, and all other geo-registered tools in a fixed position; e) changing the size, shape, and color of the 3D cursor, such as using the multi-function tool to pinch the 3D cursor to make it smaller; e) invoking filtering, segmentation, sequencing, statistical, and reporting operations, which can be performed via a variety of geo-registered tools; f) invoking pointer and movement control thereof, such as affixing the virtual pointer to the focal point pen so that as the radiologist moves the geo-registered 3D pen that he/she is holding in his/her hand, so does the virtual pointer moves through space in the virtual images projected on the head display unit; g) performing virtual cutting by moving the geo-registered cutting tool, which is linked to a virtual scalpel; h) performing virtual movement of a geo-registered catheter which is linked to a virtual catheter.

Any combination of the components and steps could be combined. Examples may include:

a) the medical personnel moving the geo-registered 3D cursor within the geo-registered 3D volumetric data to a volume of interest; b) copying and capturing data within the geo-registered 3D cursor; c) transporting the captured volume to and affixing this data to the pedestal/platform; d) medical personnel picking up the pedestal/platform (i.e., a geo-registered physical object to be held in the hand of medical personnel), turning, tilting, rotating, bringing closer/further away during examination of contents; e) picking up the focal point pen platform (i.e., a geo-registered physical object to be held in the hand of medical personnel) with the other hand, pointing to an element of the transported 3D contents, and drawing an arrow to this element; f) sending contents to report file; g) laying down the focal point pen and pick up knife; h) using the knife, dissecting the contents on the platform; and i) sending the dissected contents to the report file.

Some implementations comprise converging the left and right eyes to a single convergence/focal point through adjusting the display to account for extra-ocular muscle movements to change the look angle of the eye and accommodation to change the shape of the lens/pupil of the eye as it relates to the field of view (See U.S. Pat. No. 9,349,183, which is incorporated by reference). Process steps may comprise one or more of the following: a) occluding/eliminating the left portion of the display and associated voxels which would have been displayed with additional voxels displayed on the right portion of the display, if looking straight ahead, and similarly for the right eye occluding/eliminating the right portion of the display; b) shifting the display of the convergence/focal point to the right of the center point of the display proportional to the angular change based on distance of the view point from the convergence/focal point, similarly shifting the convergence/focal point to the left for the right eye; and c) reducing the total voxels displayed for both eyes to reflect changes in the field of view when observing a close object (i.e., accommodation).

The pixel display of the HDU may be variable in terms of the angular resolution per pixel.

This altering angular field of view could change in a step-wise fashion or in a non-linear fashion. Accompanying changes in brightness could be used to highlight the region of different resolution bands. Nominally, the high-resolution band would be associated with the fovea region. The location of the high-resolution band could vary based on the location of the focal point pen within the overall display.

In some implementations, fixed focal point spots can be placed within the volumetric images to help the radiologist focus on critical structures. In switching from one focal point spot to the next, the radiologist's eyes can jump from spot to spot via saccadic eye movements.

In some implementations, a mobile focal point spot can be placed within the volumetric images to help the radiologist focus on critical structures in a more comprehensive manner than jumping from one spot to the next. The movements of the focal point spot can be directed by an artificial intelligence algorithm or via radiologist-directed control of the virtual pointer or the focal point pen. Note that the virtual pointer is a virtual object whereas the focal point pen is a tangible object. Both of these objects operate in virtual space.

In some implementations, an electronic database of known pathology is called upon for comparison with an unknown pathology lesion from the patient's current scan. A known pathology dataset could be built and called upon. The volumetric dataset is used to generate a 3D image in a virtual cursor of the pathology affixed to a second geo-registered platform. Multiple different virtual pathologies can be placed on multiple individual geo-registered platforms for teaching purposes as well as examination purposes.

In some implementations, software to geo-register the above components and operate the system during an examination is included.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 17A and 17B illustrate a visual representation of convergence.

FIGS. 18A, 18B, 18C, and 18D FIG. 18 illustrate a method of helping the radiologist in search pattern via utilization of saccades search technique.

DETAILED DESCRIPTION

Some aspects, features and implementations described herein may include machines such as computers, electronic components, radiological components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
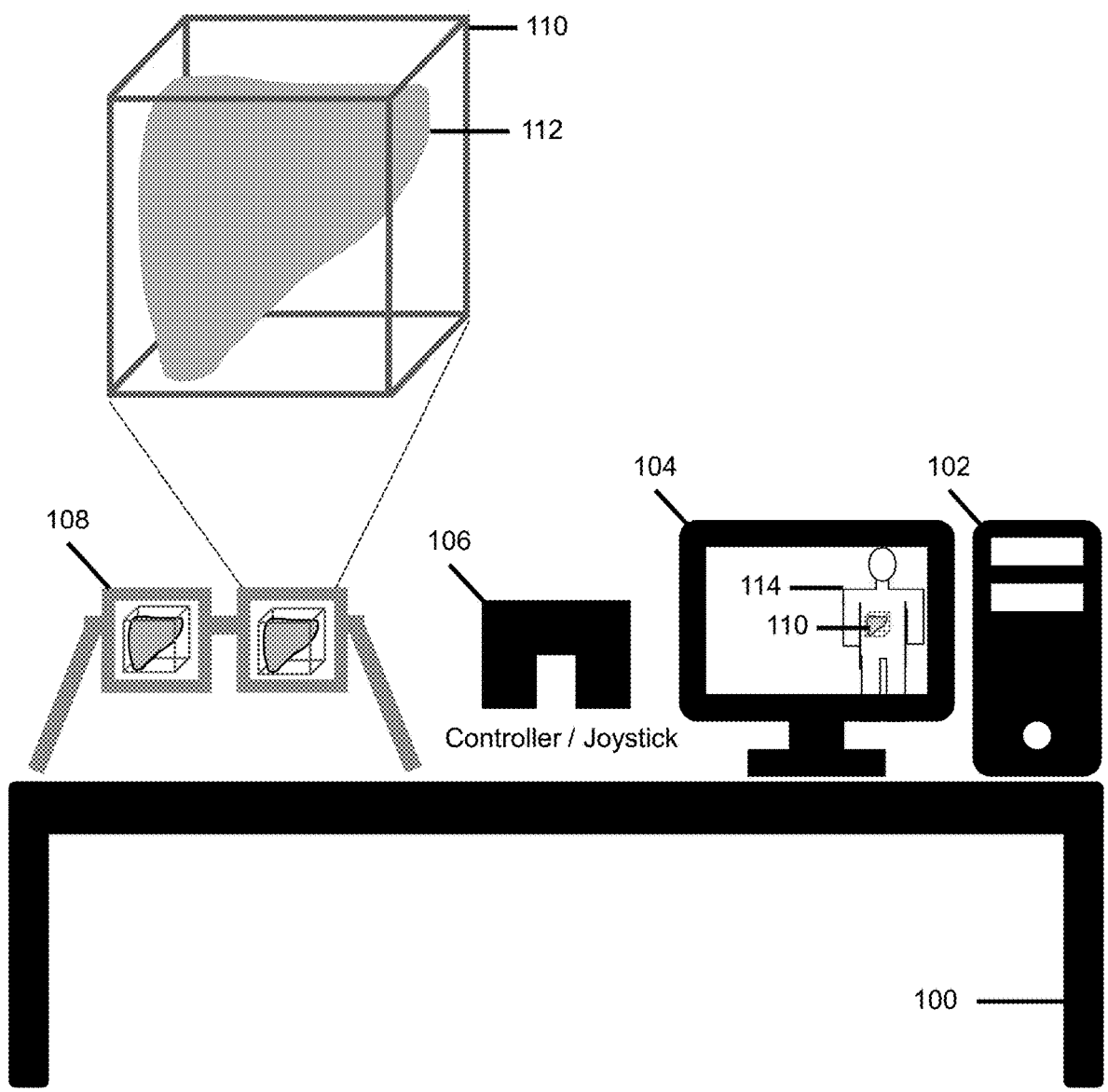
FIG. 1 illustrates presentation of a three-dimensional (3D) medical image by a HDU (head display unit).

FIG. 1 illustrates a virtual image displayed in a HDU (head display unit) 108. The radiologist's workstation will include a desk 100, a computer system 102, a diagnostic monitor 104, a controller 106 and a head display unit (HDU) 108. The HDU 108 can display a 3D cursor 110 which contains a sub-volume of interest 112. In this illustration, the diagnostic monitor is displaying a figure of a person with the 3D cursor 110 located over the right upper quadrant of the abdomen. The virtual image presented by the head display unit 108 includes a representation of the 3D cursor 110 and tissues within the volume of the 3D cursor, e.g. a liver. In a current "digital world" scenario the head display unit lacks position and orientation tracking. To manipulate the images, options beyond the standard keyboard and mouse controls may include the use of a controller 106 and joystick 106. In a "virtual world" scenario that will be described below the head display unit has a position and orientation tracking feature so movement of the head can be used to manipulate the virtual image. Further, geo-registered tools may also be used for manipulation of the virtual image.

Figure 2:
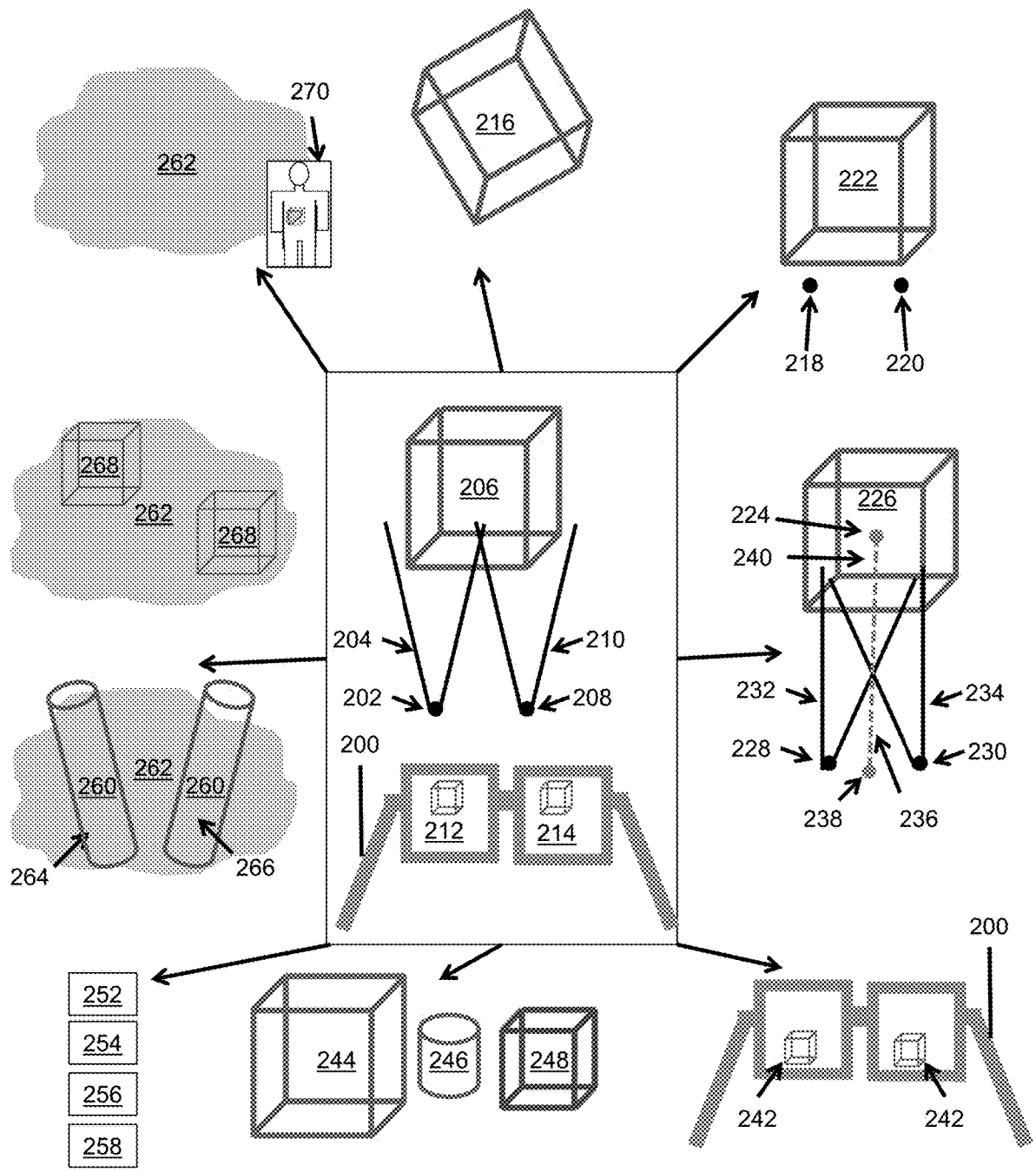
FIG. 2 illustrates aspects of manipulation of three-dimensional medical images with true stereoscopic viewing.

FIG. 2 illustrates controller/joystick inputs to provide examples of true stereoscopic 3D viewing techniques in the "digital world". In this figure, representative examples of viewing options available through the use of a hand-held controller equipped with joystick (not shown) are illustrated. In the center of the figure, the HDU 200 is shown with an initial left eye view point 202, left eye viewing angle 204 and a volume of interest 206 (e.g., volume-subtending 3D cursor) as well as a right eye view point 208, right eye viewing angle 210 and the volume of interest 206 (e.g., volume-subtending 3D cursor). Note that the HDU 200 displays the volume of interest 206 with a left eye image 212 corresponding to the left eye view point 202 and left eye viewing angle 204 of the volume of interest 206 and a right eye image 214 corresponding to the right eye view point 208 and right eye viewing angle 210 of the volume of interest 206. In the first example, controller/joystick (not shown) input can direct the 3D cursor to change orientation (roll, pitch and yaw) 216. Next, controller/joystick input can alter the distance between the left eye view point 218 and right eye viewpoint 220 with respect to the volume of interest 222. The image illustrated shows the left eye view point 218 and right eye view point 220 moved closer (i.e., zoomed in) towards the volume of interest 222. The volume of interest 222 could alternatively be moved in its coordinates toward the left eye view point 218 and right eye view point 220 to achieve the same zoomed in effect. Next, the controller/joystick (not shown) input can direct convergence to a focal point 224 shown as the orange circle within the center of the 3D cursor 226. Note the left eye viewing point 228 and the right eye viewing point 230. Also note the left eye viewing angle 232 has been adjusted based on the convergence to the focal point 224. Also note that the right eye viewing angle 234 has also been adjusted based on the convergence to the focal point 224. Further, note that a line 236 can be extending from (or close to) the midpoint of the HDU 238 to (or close to) the convergence point 224. We will refer to this line 236 as the center line of focus. Note that it would be possible to help the user focus on particular structures through implementation of the center line of focus 236. Next, controller/joystick (not shown) input can direct raising or lowering of the 3D cursor 242 within the HDU 200, or moving the 3D cursor from side to side (not shown). Next, controller/joystick (not shown) input can change the size 244, shape 246 or color 248 of the 3D cursor. Next, controller/joystick input can invoke filtering 250, segmentation 252, sequencing 254, statistical analysis 256 and reporting 258, which were discussed in USPTO application Ser. No. 15/904,092. Next, controller/joystick input can direct movement of a virtual pointer 260 through the volume of interest 262 from an initial position 264 to a subsequent position 266. The pointer 260 operates within the 3D volume 262. Movement of the pointer 260 would be controlled by person viewing the images. The pointer could vary in appearance to take on any form of one, two- or three-dimensional objects and could be programmed to move automatically without the user control. The pointer 260 is useful when smooth pursuit eye movements are necessary. For example, smooth pursuit eye movements would be beneficial when examining arteries for any blockages, wherein using the pointer 260 to trace along the length of arteries looking for blockages. Saccadian eye movement could result skipping over portions of the artery and a serious blockage go undetected; therefore, the pointer 260 could be helpful in aiding this search pattern. Multiple colored/shaped pointers 260 could be used to trace the different flows of arteries and veins. Next, controller/joystick (not shown) input can direct annotations (not shown) of one or more 3D cursors 268 within the volume of interest 262. Finally, controller/joystick input can direct icon options 270 as related to the volumetric medical imaging 262 to keep the radiologist organize in his/her checklist approach to a complex exam. Note the human body icon 270 to the display. During the course of the examination of the volume by the medical person viewing the medical images, it may be useful to quickly refer to an icon 270 in order to re-orient where exactly in the body is some tissue of interest/concern. The icon 270 would also be of utility in discussions between medical personnel. This figure shows the body in a vertical position facing forward. This icon shows: a) the current or initial viewing point relative to the human body; b) the outline of the total volume (or sub-volume) being examined; and c) approximate location of the 3D cursor(s) within the human body icon. Orientation of the body would be under the control of the medical person viewing the medical images, as would whether to display the icon 270 or not.

Figure 3:
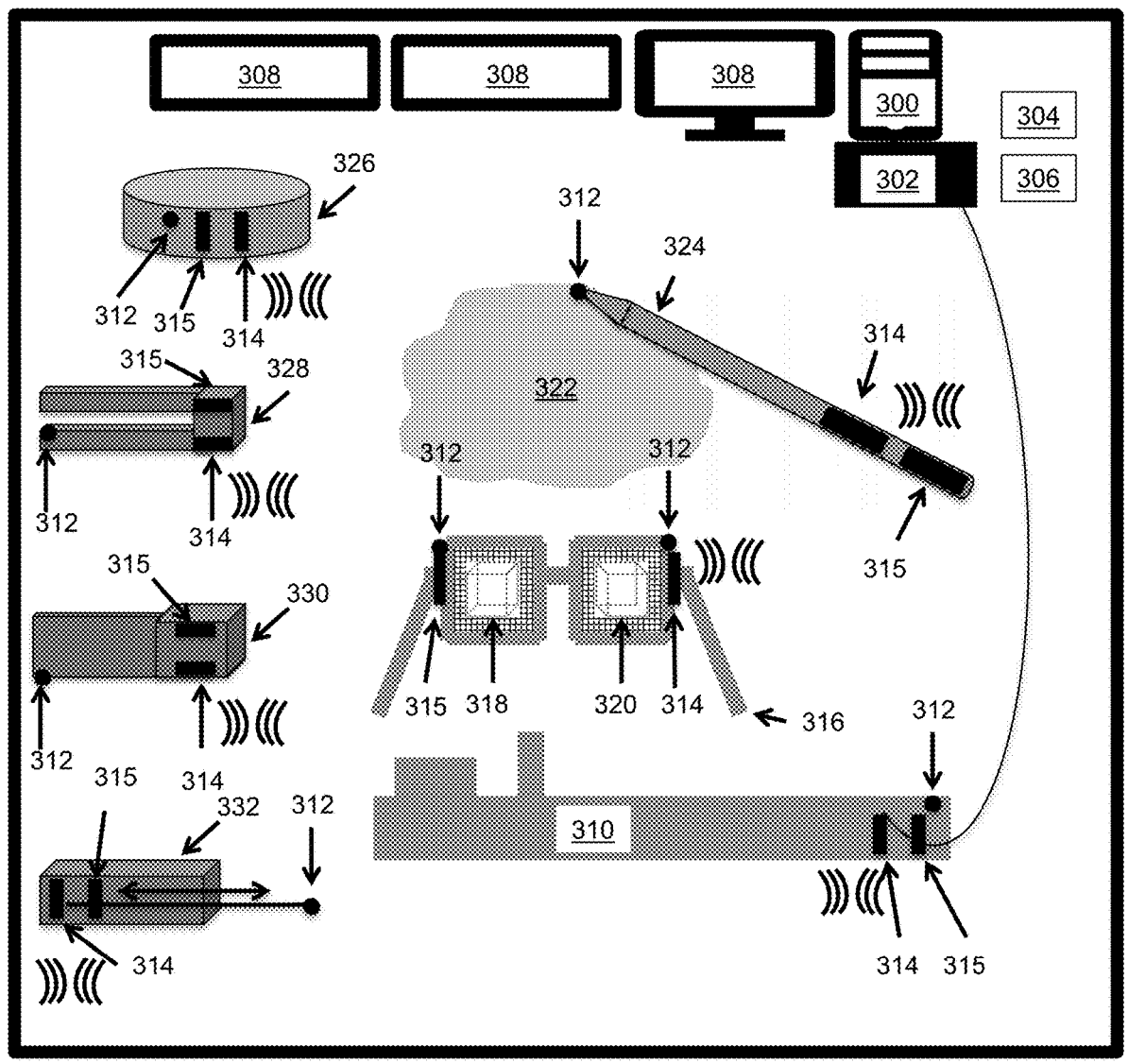
FIG. 3 illustrates a radiologist's work station that includes a plurality of geo-registered tools for manipulating three-dimensional medical images.

FIG. 3 illustrates a top down view of the radiologist's work station. In addition to standard items present at radiology work stations including a computer 300, keyboard 302, mouse 304, voice recorder 306 and monitors 308, multiple additional components are present in this patent. First, is the master control platform 310, which has registration point(s) 312 and capabilities for spatially registering each tool and other control features (e.g., raise or lower the whole imaging volume with respect to the position of the radiologist's head display unit). It has multiple buttons with multiple functions (e.g., easily toggle between control item (e.g., total volume; sub-volume; 3D cursor; and, focal point convergence) and image settings (e.g., window/leveling; and, filtering, etc.). The master control platform 310 would be equipped with a send/receive element 314 and an inertial measurement unit (IMU) 315. All other tools are spatially-registered to the master control platform 310, such that they are equipped with registration point(s) 312, a send/receive element 314 and an IMU 315 for position (i.e., translation in the x-direction, y-direction or z-direction) and orientation (i.e., roll, pitch and yaw) tracking. Next, is the HDU 316 (e.g., augmented reality, virtual reality, mixed reality) also equipped with registration point(s) 312, send/receive element 314, an IMU 315 and a left eye image 318 and a right eye image 320. Next, is the virtual image 322, which appears as a floating 3D volume in front of the radiologist as a virtual image on the HDU 316. Next, is the focal point pen 324, which is directed into the virtual image. This can be used for efficient interaction with the image, such as selecting objects, guiding focal point convergence, write notes, place symbols, etc. As with the other tools, the focal point pen is also equipped with registration point(s) 312 and a send/receive element 314 and an IMU 315. Fifth, is the geo-registered platform 326, which can be used to move a sub-volume in any position or orientation (e.g., place an unknown mass inside of a 3D cursor and onto the hand-held geo-registered platform, then move the object to a position that is best suited for close inspection such as 15 inches away from the radiologist's eyes, rotate to look at the virtual object from the top, side, bottom, back, etc.). The geo-registered platform is also equipped with registration point(s) 312 and send/receive element(s) 314 and an IMU 315. Next is the hand-held multi-function tool 328, which can be used as any programmed surgical-type device (e.g., drill, retractor, etc.), which is equipped with registration point(s) 312 and send/receive element(s) 314 and an IMU. Next, is the hand-held scalpel/knife 330, which is equipped with registration point(s) 312, send/receive elements 314 and an IMU 315. Next, is the catheter device 332, which would not necessarily have to have registration point(s) 312 and send/receive element(s) 314 and an IMU 315 for position and orientation tracking, but it could if the users demand it so. Note that each item has options for wireless capabilities and battery powered. The virtual image 322 is displayed on the HDU 316, but appears as a 3D object sitting right in front of the radiologist on his desk.

Figure 4:
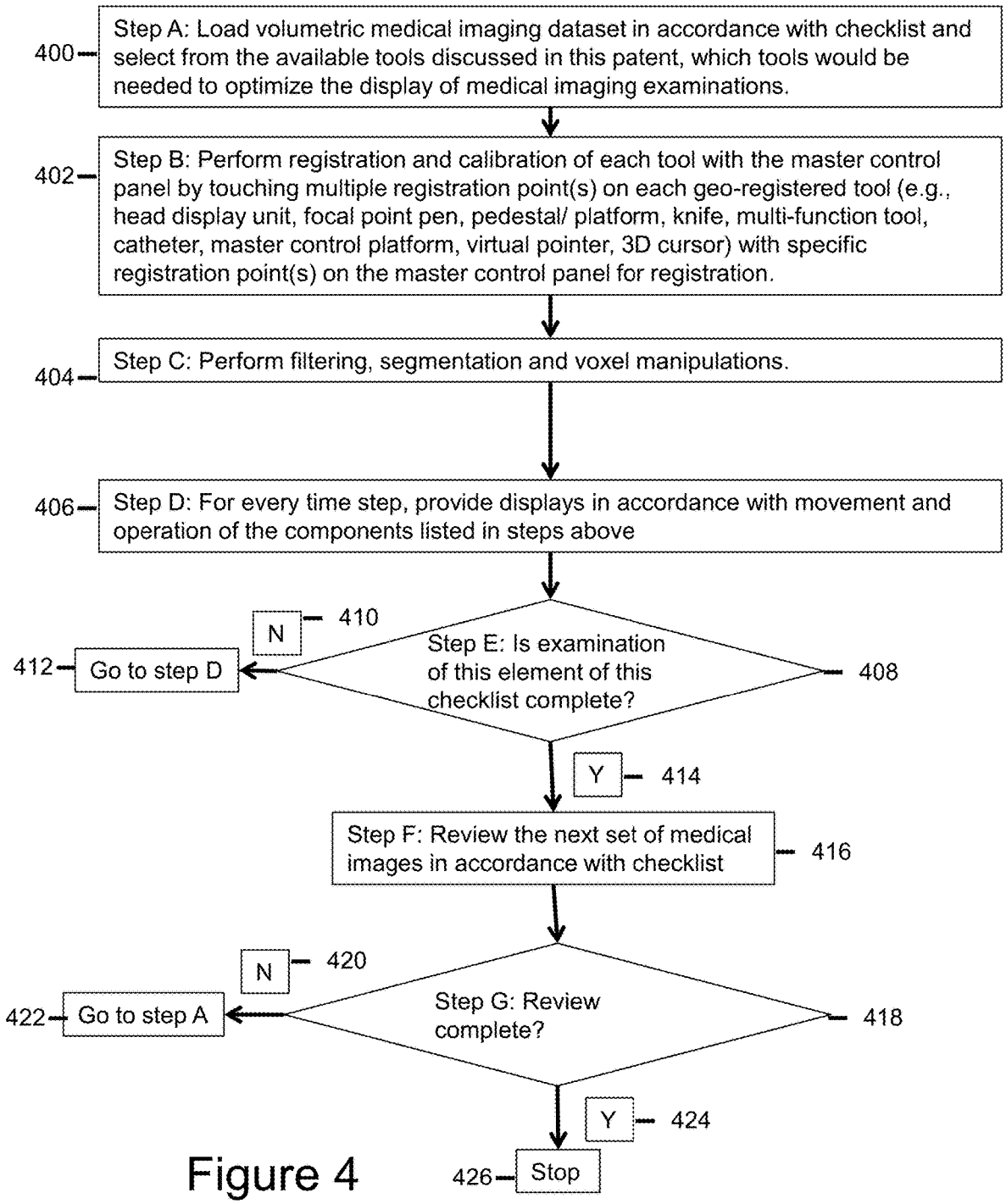
FIG. 4 is a flow diagram of steps for using geo-registered tools to manipulate three-dimensional medical images for examinations.

FIG. 4 illustrates a flow diagram for the use of geo-registered tools to optimize display of medical imaging examinations. In Step A 400, load volumetric medical imaging dataset in accordance with checklist and select from the available tools discussed in this patent, which tools would be needed to optimize the display of medical imaging examinations. In Step B 402, perform registration and calibration of each tool with the master control panel by touching multiple registration point(s) on each geo-registered tool (e.g., head display unit, focal point pen, pedestal/platform, knife, multi-function tool, catheter, master control platform, virtual pointer, 3D cursor) with specific registration point(s) on the master control panel for registration. In Step C 404, perform filtering, segmentation and voxel manipulations, e.g. as described in U.S. Ser. No. 15/904,092 and U.S. Ser. No. 16/195,251, both of which are incorporated by reference. In Step D 406, for every time step, provide displays in accordance with movement and operation of the components listed in steps above. Step E 408 is to determine if the examination of this element of this checklist complete. If the answer is no 410, then the next step 412 is to go to step D 406. If the answer is yes 414, then proceed to Step F, which is to review the next set of medical images in accordance with the checklist 416. Step G 418 is to determine if the review is complete. If the answer is no 420, then the next step 422 is to proceed to step A. If the answer is yes 424, then the stop 426.

Figure 5:
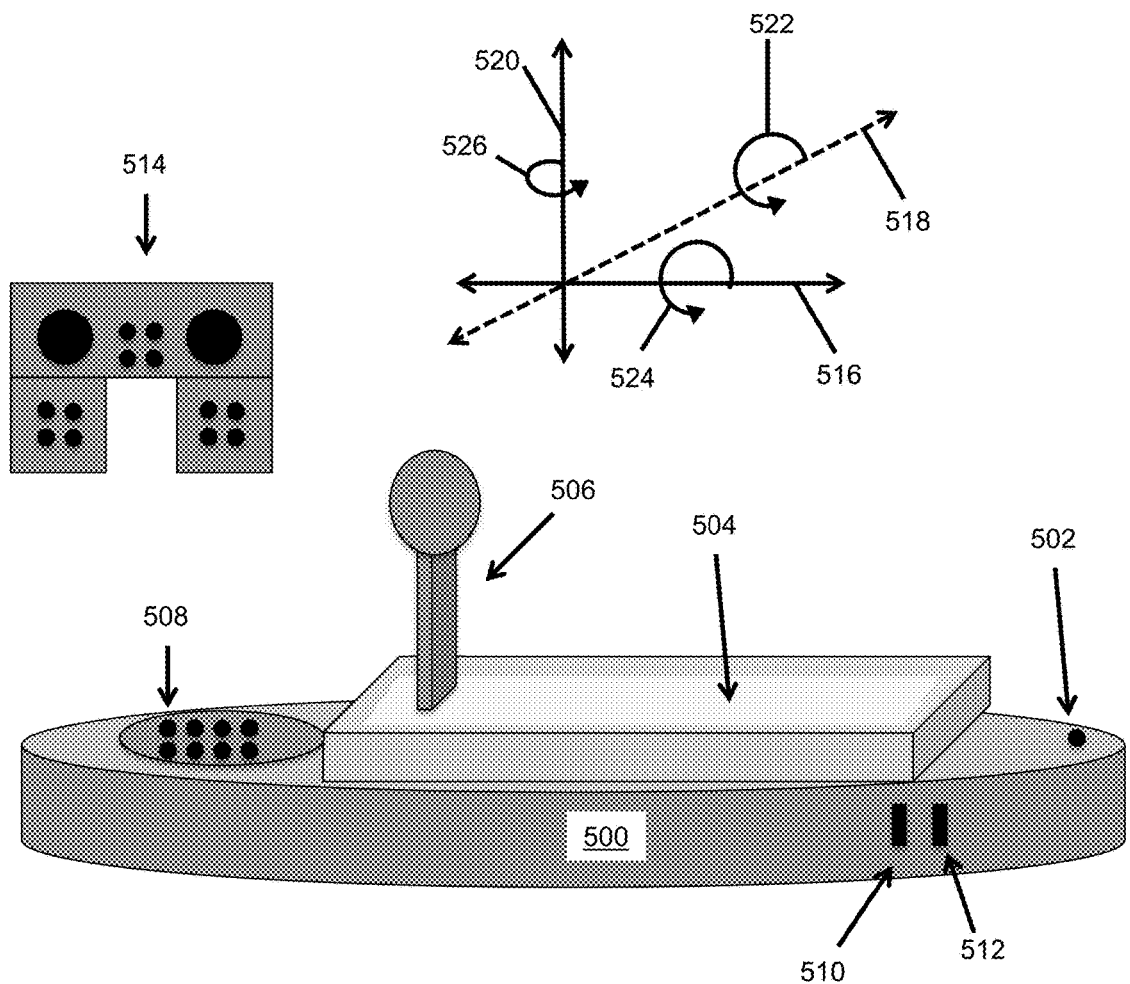
FIG. 5 illustrates the master control platform in greater detail.

FIG. 5 illustrates the geo-registration unit, which we also refer to as the master control platform. The master control platform 500 consists of the following: mount (not shown) equipped with position relative to the head display unit using a geo-registration point(s) 502; platform(s) 504 with roll 522, pitch 524 and yaw 526 and translation capability in the x-direction (i.e., side to side) 516, y-direction (i.e., forward-to-back) 518 and z-direction (i.e., up-down) 520; joystick(s) 506 with roll 522, pitch 524 and yaw 526 (RPY) and translation capability in the x-direction 516, y-direction 518 and z-direction 520; multiple buttons 508 to easily toggle between control item (e.g., total volume; sub-volume; 3D cursor; and, focal point convergence toggling) and image settings (e.g., window/leveling; and, filtering, etc.). Joystick 506 functionality includes the following: a) change the orientation of the 3D cursor roll, pitch and yaw; b) zoom the medical person viewpoint in toward the 3D cursor and out away from the cursor; c) invoke convergence; d) raise and lower the 3D cursor as to where it is displayed on the headset; e) change the size, shape, and color of the 3D cursor; e) invoke filtering, segmentation, sequencing, statistical, and reporting operations; f) invoke pointer and movement control thereof; g) annotate one or more 3D cursors within the volume of interest; h) invoke icon options. Although not mandatory, the desk geo-registration device 500 would typically be at a fixed location at the medical person's work station. Another optional component of the geo-registration unit 500 would be an additional controller 514, which would be an ergonomic controller with buttons and joysticks. The coordinate system for the medical images volume would be offset a specified distance from the desk geo-registration device 500. The registration points on the focal point pen and the pedestal/platform would physically touch the registration point(s) 502 on the desk geo-registration device during the initialization process. Key elements of the desk geo-registration device include: the geo-registration point 502; the transmit/receive unit (aka, the send/receive element) 510; battery element (not shown); and b) the IMU 512.

Figure 6:
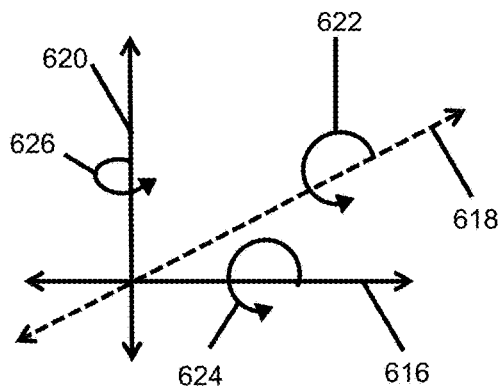
FIG. 6 illustrates the HDU in greater detail.
Figure 6:
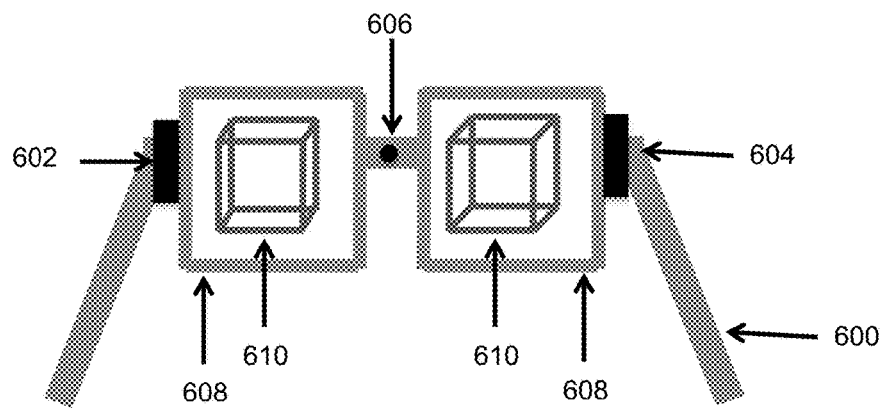

FIG. 6 illustrates the geo-registered true stereoscopic head display unit within the geo-registration coordinate system viewing a 3D cursor. The HDU 600 is equipped with an IMU 602, a transmit/receive element 604 and a geo-registration point(s) 606. Thus, for a fixed location of a 3D cursor with respect to the master control unit, a movement of the radiologist's head will alter the appearance of the 3D cursor on the HDU 600. The HDU 600 is illustrated in this figure. Key components include: an IMU 602; lenses 610 that display both the real-world scene and the virtual image 608; geo-registration point 606; battery element (not shown); and digital transmit/receive system 604. The IMU 602 senses head motion and transmits changes of head position and orientation through the transmission system to the master control platform. The computer calculates the effect of changes of head position and orientation and changes what is being displayed on the lenses and transmits the adjusted display to the HDU 600 to project on the lenses 608. What is being projected on the lenses displays is also affected by commands issued through the joystick/master control platform to the computer, and thence an updated display transmitted to the HDU 600. The geo-registration point interacts with the desk geo-registration device and is initialized with X 616, Y 618, Z 620 coordinates and orientation (i.e., roll 622, pitch 624, and yaw 626) at time of initialization. Note: these coordinates and orientation are re-computed when the medical person viewing the medical images puts on the HDU.

Figure 7:
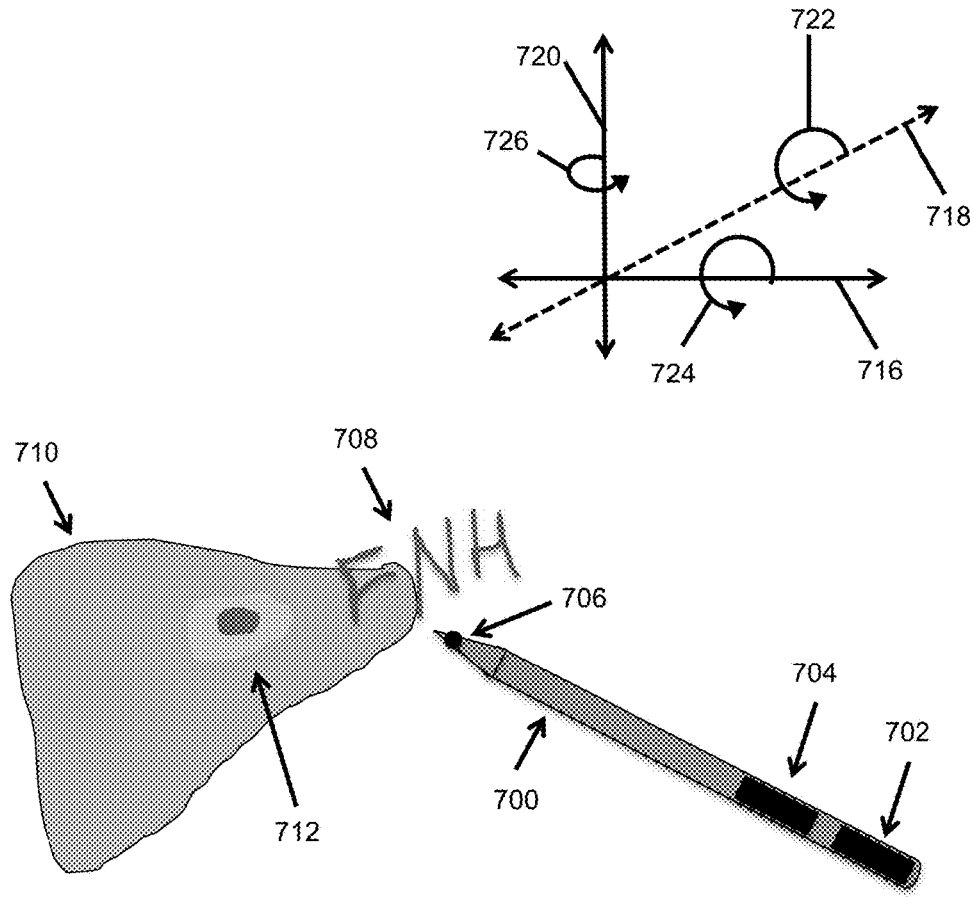
FIG. 7 illustrates the geo-registered focal point pen within the geo-registered coordinate system.

FIG. 7 illustrates the geo-registered focal point pen 142 in greater detail. The focal point pen 700 is equipped with a geo-registration point 706 at the tip, contains an IMU 702 for determining location and/or orientation, and a transmit/receive unit 704 for communication with the computer. The focal point pen 700 can be moved within the 3D volume and point to anomalous tissue 712 and inscribe notes 708 within 3D space, but typically adjacent to the volume of interest 710 for future reference and to place it into the report. The geo-registration point 706 interacts with the master control platform and is initialized with X 716, Y 718, Z 720 coordinates and orientation (i.e., roll 722, pitch 724, and yaw 726) at time of initialization. Note: these coordinates and orientation are re-computed when the medical person viewing the medical images puts on the HDU. The focal point pen 700 which is an actual, tangible object in the shape of a pen (or other actual object that could be used for pointing) would be held by medical person viewing the medical images, which would interact with the virtual medical images. (Note that the focal point pen 700 is geo-registered with the medical images 710.) This interaction includes actually physically moving the focal point pen 700 in the air in front of the medical person viewing the medical images 710 and, simultaneously, be moving the focal point pen 700 through virtual space showing the 3D volumetric medical image 710. The display would show a virtual pen (not shown) properly geo-registered within the 3D medical image. If there is mis-registration between the tangible focal point pen 700 and the virtual focal point pen (not shown), the focal point pen 700 could be moved back to the master control platform for re-registration for a process including touching the registration points(s) 706 of the focal point pen to the registration point of the master control platform (not shown). There is a wide array of uses for the focal point pen which would include, but not be limited to, the following: moving the focal point pen 700 within the 3D image set so as to follow arteries/veins within a complex vascular structure; touching a point within the 3D image set with the tip of the focal point pen 700 for annotation and/or cross reference the a particular 2D image slice; writing notes, drawing symbols (e.g., encircle tissue of concern with a sphere; draw arrows); and, illustrating a potential cut path for surgical planning.

Figure 8:
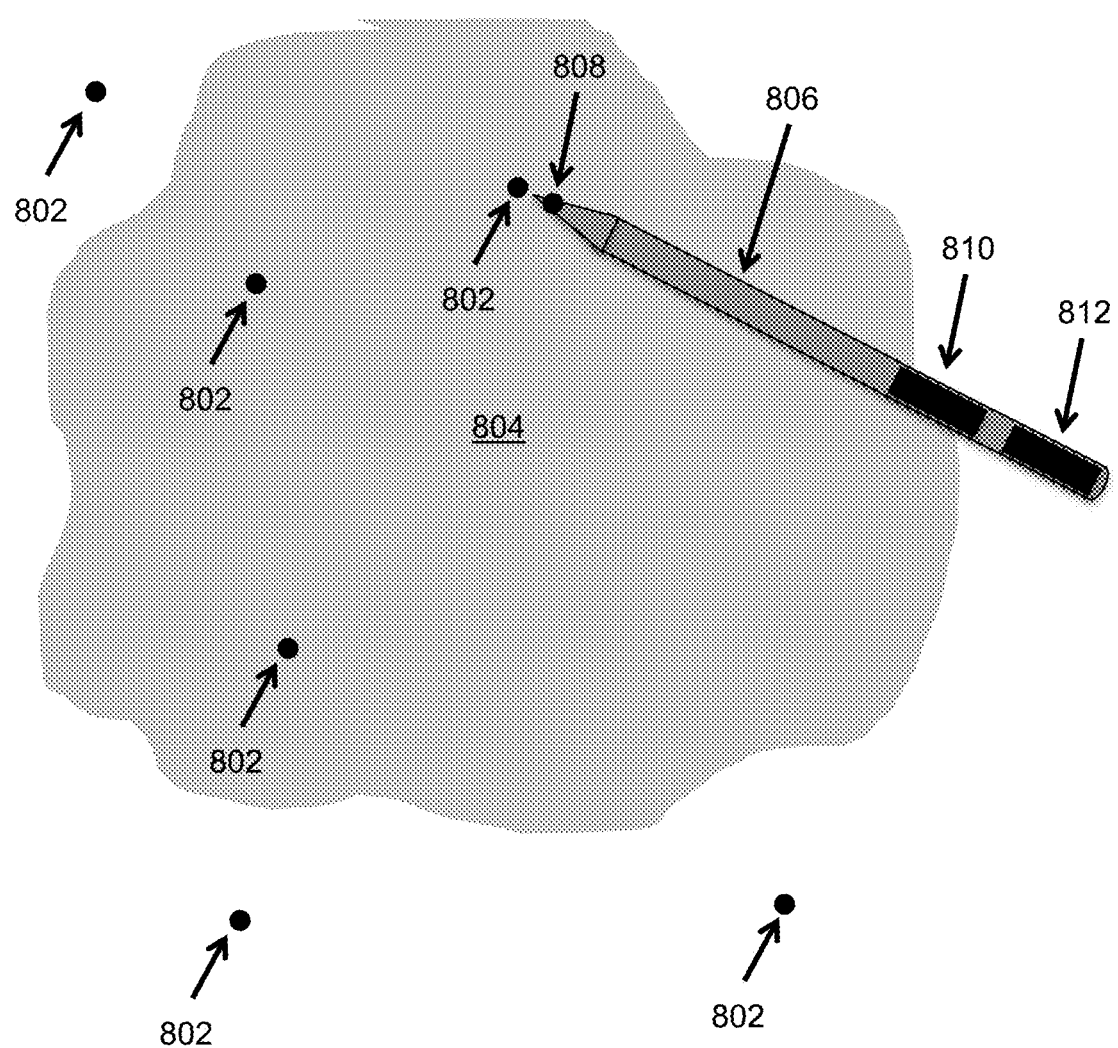
FIG. 8 illustrates multiple calibration points within the geo-registration coordinate system.

FIG. 8 illustrates multiple calibration points within the geo-registration coordinate system. In this figure, the focal point pen 806 is illustrated touching the location of each of one of the calibration points 802, which can be inside or outside of the imaging volume 804. Note that the focal point pen 806 has a registration point 808, an IMU 810 and a transmit/receive unit 812.

Figure 9:
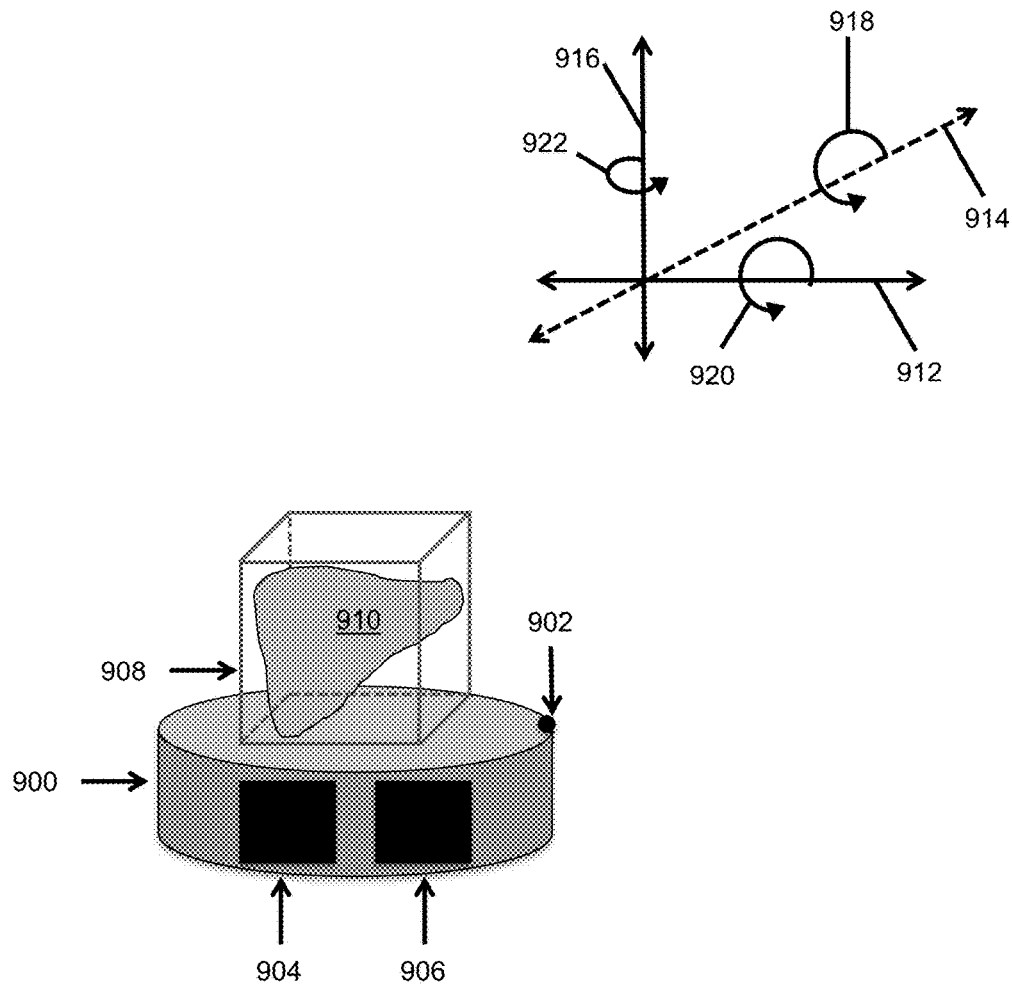
FIG. 9 illustrates the geo-registered hand-held pedestal within the geo-registration coordinate system.

FIG. 9 illustrates the hand-held pedestal within the geo-registration coordinate system. The hand-held pedestal 900 has a geo-registration point 902, an IMU 904 and transmit/receive unit 906, which updates the system with regard to its location and orientation. The location of the pedestal can be changed (up/down/left/right/forward/back) and its orientation (roll, pitch and yaw). This overcomes the difficulty and non-intuitive interfaces with medical imaging including keyboard, mouse, button on joystick, etc. The radiologist can use a 3D cursor 908 with copied contents 910, affix it to the pedestal/platform and, transport it to a new location in front of him/her. The geo-registration point 902 interacts with the desk geo-registration device and is initialized with X 912, Y 914, Z 916 coordinates and orientation (i.e., roll 918, pitch 920, and yaw 922) at time of initialization. Note: these coordinates and orientation are re-computed when the medical person viewing the medical images puts on the HDU. The pedestal/platform 900 which is an actual tangible object, such as in the shape of a cell phone (or other actual object that could be used for holding a virtual object) would be held by medical person viewing the medical images which would interact with the virtual medical images. While a geo-registered tool with geo-registration point(s) 902, an inertial measurement unit 904 and transmit/receive unit is preferred 906, an alternative embodiment would be to use a set of cameras (e.g., located on the HDU or elsewhere in the room) for object tracking. (Note that the pedestal/platform 900 is geo-registered with the medical images.) This interaction includes actually moving pedestal/platform 900 the air in front of the medical person viewing the medical images and, simultaneously, be moving the pedestal/platform 900 through virtual space showing the 3D volumetric medical image. The display would show a virtual pedestal/platform 900 properly geo-registered within the 3D medical image. There is a wide array of uses for the pedestal/platform 900 which would include, but not be limited to, the following: moving the pedestal/platform 900 to a volume of interest within the 3D medical image (e.g., volume 910 contained within the 3D cursor 908) by hand movements of the pedestal/platform 900 and then the medical person viewing the medical images issues command to affix the volume of interest 910 inside the 3D cursor 910 to the pedestal/platform 900. Note: once the volume 910 was affixed to the pedestal/platform 900, the volume of interest 910 would move, corresponding to and as the pedestal/platform 900 was moved. Thence, the medical person viewing the medical images by hand control of the pedestal/platform 900 could rotate, tilt the pedestal/platform 900 for examination. Further, this examination process could be accompanied by head movements by medical person viewing the medical images to obtain a better perspective of any tissue of potential concern. This process allows one to examine a medical imaging dataset the same way that he/she has spent a lifetime examining hand-held objects, such as a studying the stitches on baseball/softball. The volume on the pedestal/platform 900 would return to the original position on the command of the medical person. Note: battery in this element is not shown.

Figure 10A:
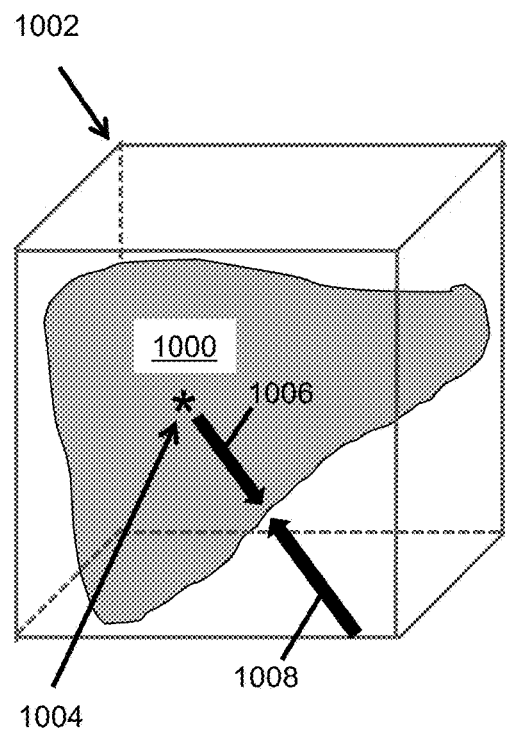
FIG. 10A, 10B, 10C and 10D illustrate an ablative process to aid in searching the internal structure and any abnormalities of an organ.
Figure 10B:
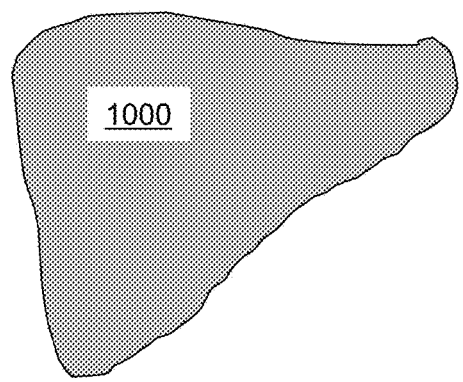
Figure 10C:
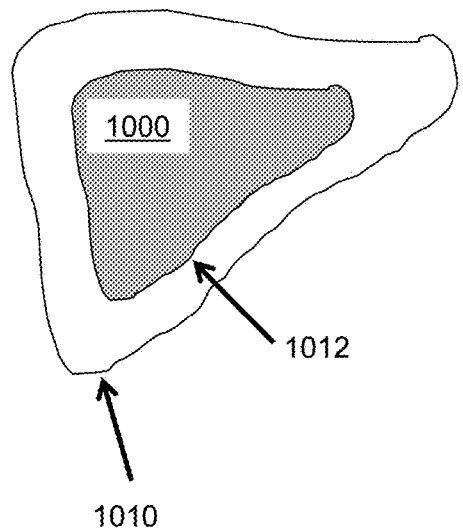
Figure 10D:
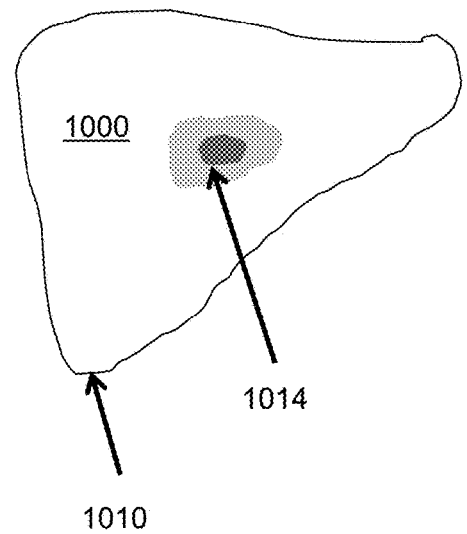

FIG. 10A, 10B, 10C and 10D illustrate an ablative process to aid in searching the internal structure and any abnormalities of an organ. FIG. 10A illustrates an organ 1000 contained within the 3D cursor 1002. To achieve the outer shell of the organ inside the 3D cursor, one can perform a segmentation process to isolate the organ 1000. Then, the surface layer of voxels can be eliminated, beginning the ablation process. The surface layer of voxels can be identified by going from either the center voxel of the organ 1004 in the outward direction 1006 toward the boundary of the 3D cursor 1002 and analyzing voxel properties to determine to voxel at the surface. Alternatively, the surface layer of voxels can be identified by going from the boundary of the 3D cursor 1002 in the inward direction 1008 towards the center voxel of the organ 1004 and analyzing voxel properties to determine the voxel at the surface. FIG. 10B shows the organ of interest 1000 without the 3D cursor 1002. FIG. 10C sequentially removes voxels from outer shells 1002 of the organ 1000 in a step-wise fashion. The original outer surface 1010 is shown. Also, the new outer surface 1012 after ablation of N steps is shown. FIG. 10D shows an abnormality 1014 within the confines of the organ 1000. During each ablative step, normal organ tissue would be ablated away, but abnormal liver tissue would remain. In this example, an illustration of a liver lesion called a focal nodular hyperplasia (FNH) 1014 is shown, but all remaining normal liver tissue is disappeared. For orientation, the original outer surface 1010 is shown.

Figure 11:
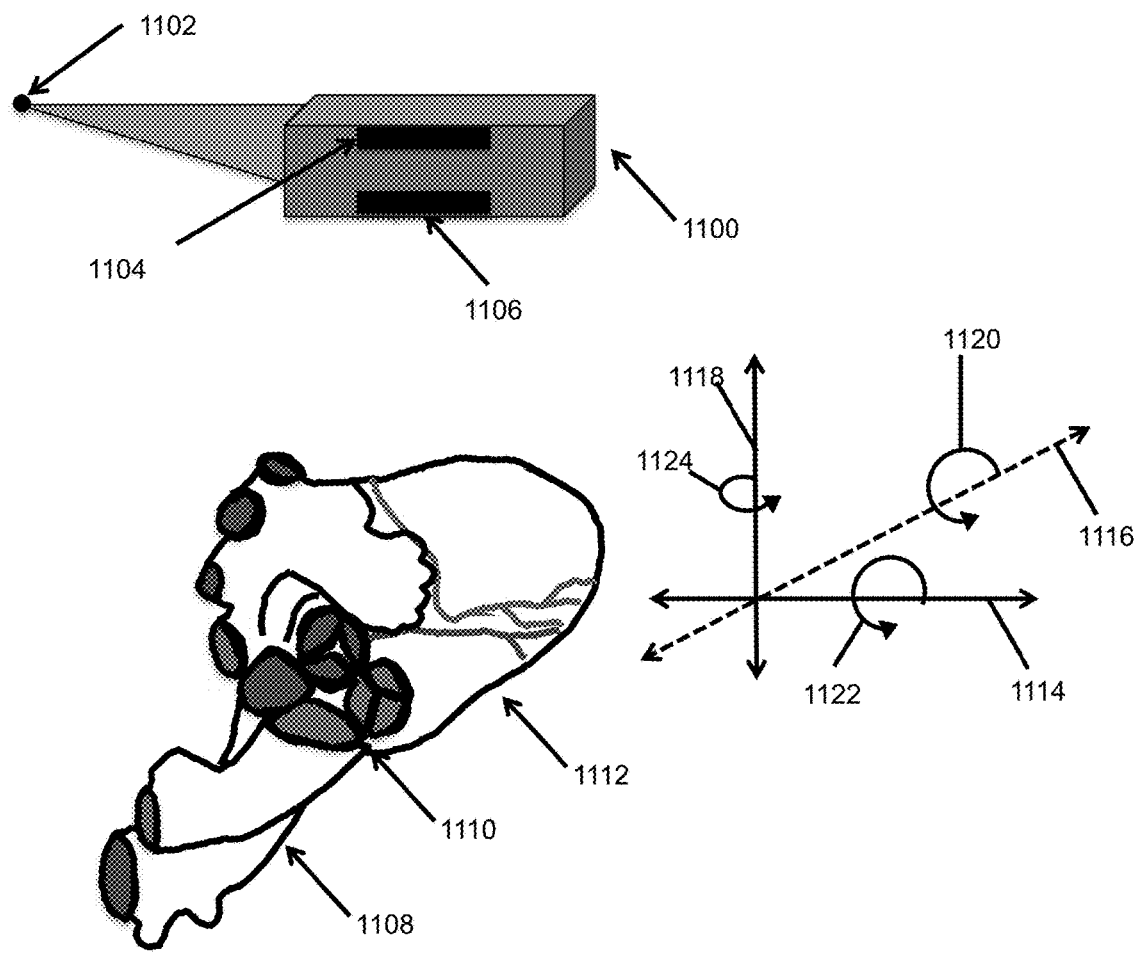
FIG. 11 illustrates a geo-registered knife used to dissect tissues within the geo- registration coordinate system.

FIG. 11 illustrates a geo-registered knife and how it could be used to carve away a portion of a heart. The geo-registered knife 1100 contains a registration point 1102, a transmit/receive element 1104 and an IMU 1106. The knife 1100 is a physical object and its position and orientation can be changed by the radiologist. The knife 1100 has the properties of being able to dissect the virtual images and remove them in order to better view the internal structure of the tissue at hand. For example, the great vessels 1108 could be cut along a cutting plane 1110 and rotated away from the remainder of the heart 1112. The coordinates of the cutting surface can be determined by the user. The geo-registration point interacts with the desk geo-registration device and is initialized with X 1114, Y 1116, Z 1118 coordinates and orientation (i.e., roll 1120, pitch 1122, and yaw 1124) at time of initialization. Note: these coordinates and orientation are re-computed when the medical person viewing the medical images puts on the HDU. Note: battery in this element is not shown.

Figure 12:
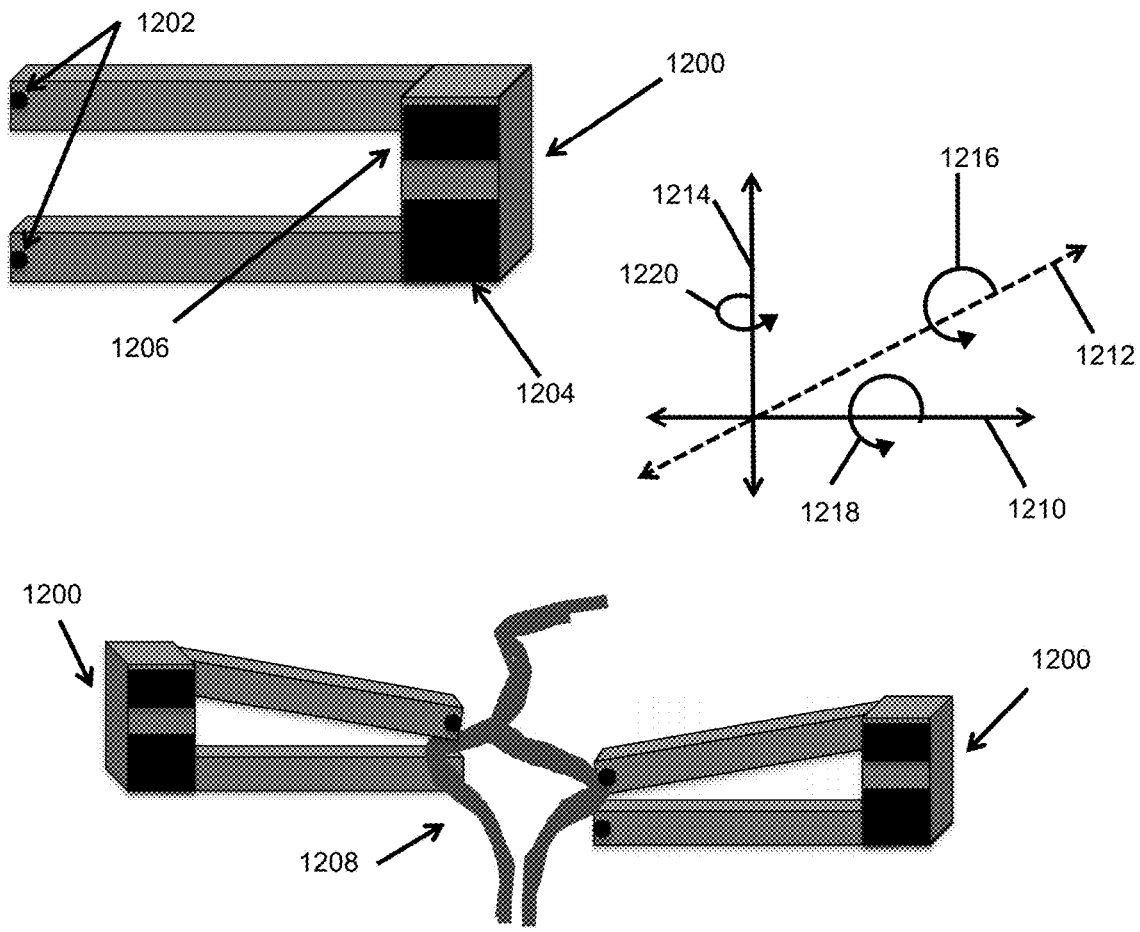
FIG. 12 illustrates a geo-registered multi-function tool used to manipulate voxels within the geo-registration coordinate system.

FIG. 12 illustrates a geo-registered multi-function tool used to manipulate voxels within the geo-registration coordinate system. The geo-registered multi-function tool 1200 is equipped with registration points 1202, an IMU 1204 and a transmit/receive unit 1206. The primary use of the geo-registered multi-function tool 1200 is expected to be grabbing tool that can manipulate and hold tissue (i.e., a set of voxels) in place. Other surgical instruments, such as drill, hammer, screw, scalpel, etc. can also interface with the tool. As illustrated, two multifunction tools are being used to pull apart two closely spaced blood vessels 1208 with voxel manipulations performed in accordance with U.S. patent application Ser. No. 62/695,868, which is incorporated by reference. The geo-registration point interacts with the desk geo-registration device and is initialized with X 1210, Y 1212, Z 1214 coordinates and orientation (i.e., roll 1216, pitch 1218, and yaw 1220) at time of initialization. Note: these coordinates and orientation are re-computed when the medical person viewing the medical images puts on the HDU. Note: battery in this element is not shown.

Figure 13:
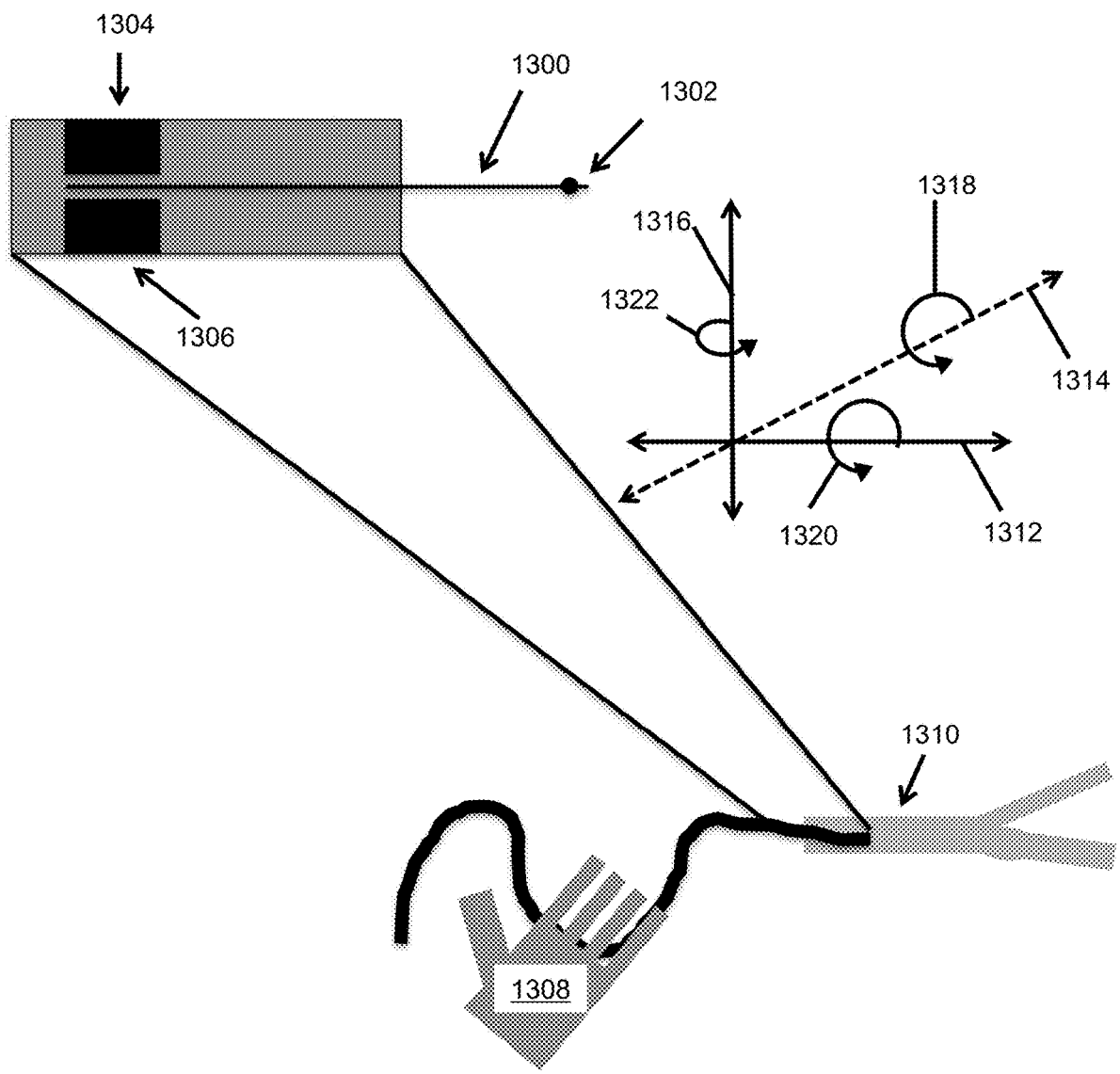
FIG. 13 illustrates the geo-registered catheter with navigation through a blood vessel.

FIG. 13 illustrates the geo-registered catheter with navigation through a blood vessel.

The geo-registered catheter 1300 consists of a tubular structure with a wire entering into it. The geo-registered catheter has a registration point 1302, an IMU 1304 and a transmit/receive unit 1306. The user's hand 1308 would insert the catheter 1300 into the virtual image and continuously push it up through the vascular system 1310. Each succeeding element of the catheter goes to the location and orientation of the immediately proceeding (or trailing) element as the radiologist pushes, pulls or twists the catheter. Similarly, the virtual catheter would be able to move through the virtual image via translation in the X 1312, Y 1314 or Z 1316 coordinates or via roll 1318, pitch 1320 and yaw 1322. This could aid in pre-operative planning or facilitate training interventional operations. Note: battery in this element is not shown.

Figure 14:
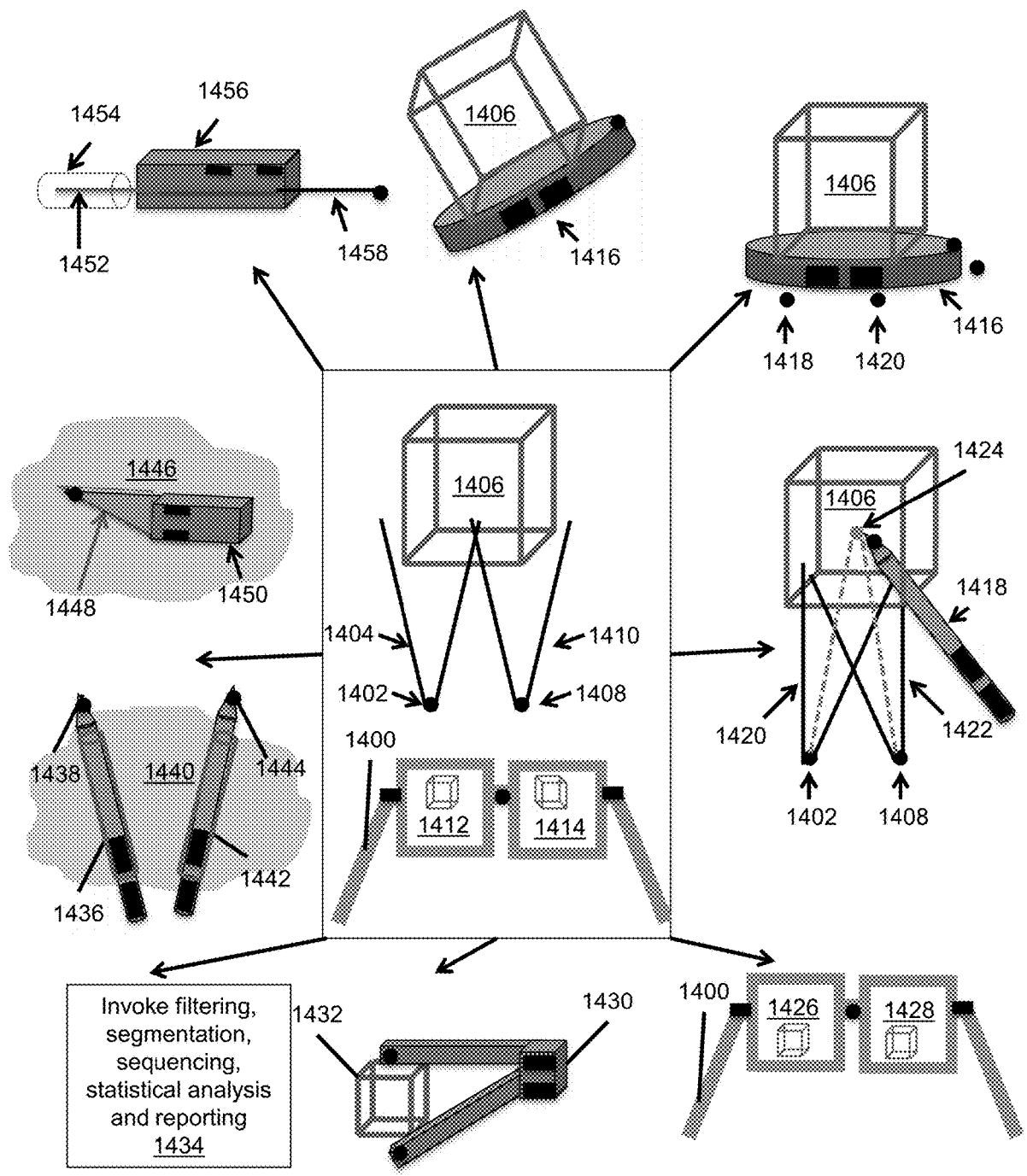
FIG. 14 illustrates the geo-registered tool inputs to provide examples of true stereoscopic 3D viewing techniques in the "virtual world".

FIG. 14 illustrates geo-registered tool inputs to provide examples of true stereoscopic 3D viewing techniques in the "virtual world". In the center of the figure, the HDU 1400 is shown with an initial left eye view point 1402, left eye viewing angle 1404 and a volume of interest 1406 (e.g., volume-subtending 3D cursor) as well as a right eye view point 1408, right eye viewing angle 1410 and the volume of interest 1406 (e.g., volume-subtending 3D cursor). Note that the HDU 1400 displays the volume of interest 1406 with a left eye image 1412 corresponding to the left eye view point 1402 and left eye viewing angle 1404 of the volume of interest 1406 and a right eye image 1414 corresponding to the right eye view point 1408 and right eye viewing angle 1410 of the volume of interest 1406. In the first example, the orientation of the 3D cursor 1406 changes (i.e., change in roll, pitch or yaw) via moving of the hand-held geo-registered platform 1416 temporarily attached to the 3D cursor 1406. If the radiologist had the image of the heart affixed to the 3D cursor 1406, then the radiologist could hold the platform 1416 and look at the heart from the top, bottom, left and right sides, front and back. This would provide intuitive controls for viewing an object. Next, the left eye viewpoint 1418 and right eye viewpoint 1420 have been moved in toward the 3D cursor 1406, such as the user wearing a HDU 1400 with head tracking capabilities physically leaning forward closer to the platform 1416. Please note that the initial distance between the left eye viewing point 1402 and right eye viewing point 1408 and the 3D cursor 1406 has been changed. Alternatively, a similar visual effect could be achieved via physically moving the platform 1416 and the 3D cursor 1406 affixed to it closer to the HDU 1400. Thus, movement of the HDU 1400 or platform 1416 could alter the viewing of the 3D cursor 1406. Next, if the radiologist wanted to take a closer inspection through the volume of interest as defined by the 3D cursor 1408, he could move the focal point pen 1418 in front of him, such that the tip of the focal point pen 1418 is a convergence point 1424. Note that the left eye viewing angle 1420 and right eye viewing angle 1422 have changed when compared with the initial left eye viewing angle 1402 and initial right eye viewing angle 1408 in accordance with the focal point convergence, as described in U.S. patent applications Ser. No. 12/176,569 and 14/313,398 which are incorporated by reference. Next, the radiologist might decide to raise and lower the 3D cursor as to where it is displayed on the headset. This could be accomplished by raising or lowering the radiologist's chair and keeping the radiologist's desk, master control platform, and all other geo-registered tools in a fixed position. Further, the sub-volume of interest could be separated from the rest of the volume, placed on a pedestal and raised or lowered. Further, it could be copied and affixed to the platform 1416, such that the original volumetric dataset is unaltered, but the sub- volume is copied and set aside on the platform for additional inspection/viewing. Further, a virtual pedestal could be invoked through use of the master control panel to move a sub-volume encompassed in the 3D cursor. Note that the 3D cursor is illustrated in a lower position in the left eye image 1426 and right eye image 1428 in the HDU 1400, compare with the position of the 3D cursor in the initial left eye image 1412 and initial right eye image 1414. Next, the radiologist could change the size, shape, and color of the 3D cursor, such as using the geo-registered multi-function tool 1430 to pinch the 3D cursor 1432 to make it smaller. The master control platform and other geo-registered tools could also accomplish this. Next, the radiologist could invoke filtering, segmentation, sequencing, statistical, and reporting operations 1434, which can be performed via a variety of geo-registered tools. Next, the radiologist could invoke pointer movement control thereof, such as affixing the virtual pointer 1436 to the focal point pen 1438 so that as the radiologist moves the geo-registered focal point pen 1438 that he/she is holding in his/her hand, so does the virtual pointer 1436 moves through space in the virtual images 1440 projected on the head display unit. Note that new position of the focal point pen 1444 and the new position of the virtual pointer. Next, the radiologist could perform cutting through moving the geo-registered cutting tool 1450, which is linked to a virtual scalpel 1448 through the volume 1446 to perform virtual dissection. Note that many of these techniques may include voxel manipulations, which may be implemented as described in U.S. patent application Ser. No. 62/695,868 which is incorporated by reference. The final example provided in this figure is for the radiologist to perform movement of a geo-registered catheter 1458 associated with the geo-registered catheter supporting device 1456, which is linked to a virtual catheter 1452 inside of a virtual blood vessel 1454, which could be used to perform dry runs/pre-operative planning sessions.

Figure 15A:
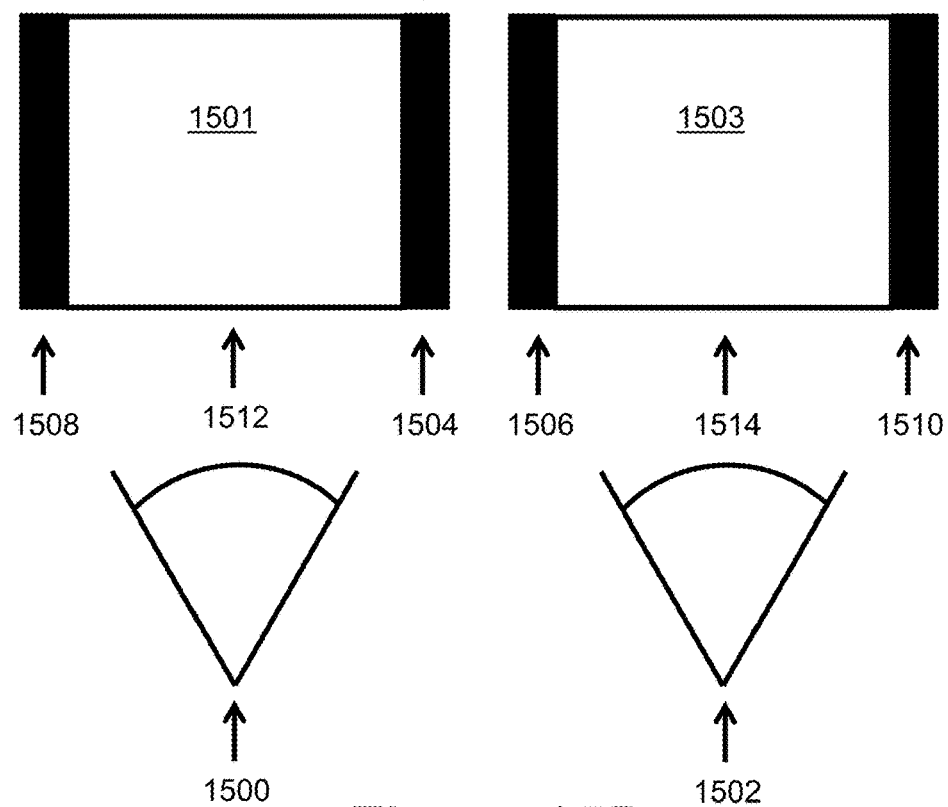
FIGS. 15A and 15B illustrate digital convergence of the head display unit to a focal point.
Figure 15B:
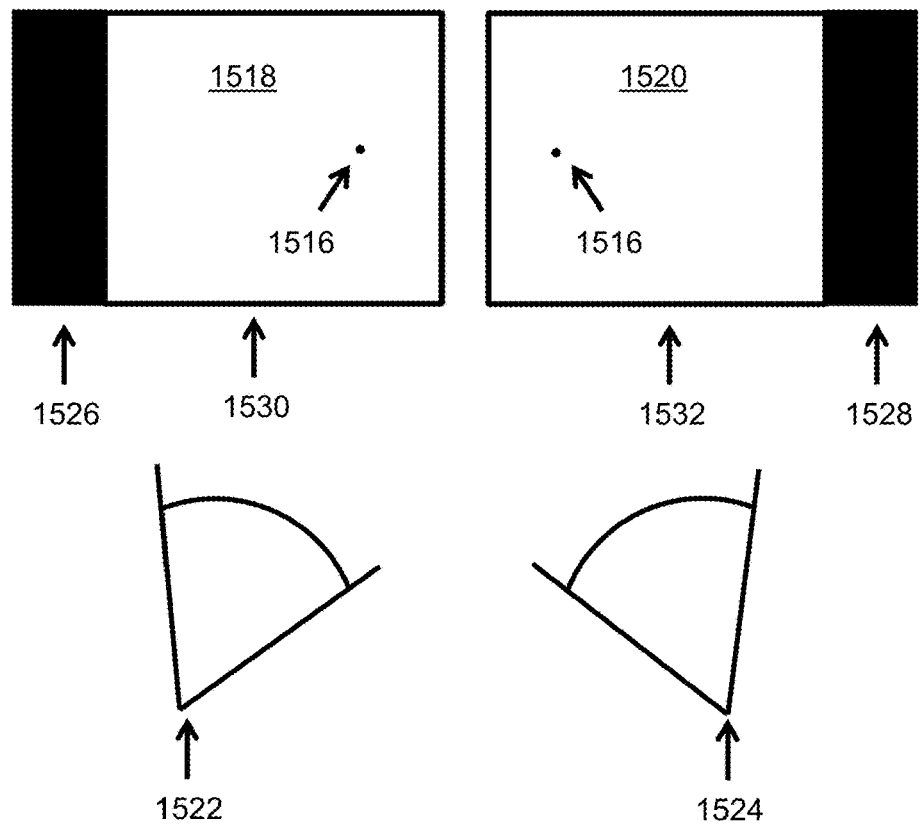

FIGS. 15A and 15B illustrate digital convergence of the head display unit to a focal point. Key binocular depth components include stereopsis, convergence and accommodation. This figure illustrates improving the binocular depth component by employing convergence, such that both eyes converge to a single focal within the medical image. The key advantages of convergence is that this process replicates how the eyes have been trained over one's lifetime to examine a small area to better understand its structure. When examining medical images this is particularly useful when medical personnel examine small tumors, heart valves, aneurysms, etc. This figure illustrates a process to replicate the process of the human eyes when converging to focus on a specific spot but, instead, with 3D medical images. The extra-ocular muscles of the eye control the eye movement and direction. In order to provide convergence to a focal point, some aspects of the left and right eye displays could be turned on and other aspects of the left and right eye displays could be turned off. In FIG. 15A, assume that an individual is looking straight ahead to a point at an infinite distance. The orientation of the left eye 1500 and right eye 1502 are parallel. Note that portions 1504 of the medial side of the left eye display 1501 are turned off and are shown in black, which may account for a small amount (e.g., less than 10 degrees of the horizontal field of view). Note that portions 1506 of the medial side of the right eye display 1503 are turned off and are shown in black, which may account for a small amount (e.g., less than 10 degrees of the horizontal field of view). Note that portions 1508 of the lateral side of the left eye display 1501 are turned off and are shown in black, which may account for a small amount (e.g., less than 10 degrees of the horizontal field of view). Note that portions 1510 of the lateral side of the right eye display 1503 are turned off and are shown in black, which may account for a small amount (e.g., less than 10 degrees of the horizontal field of view). Note that portions 1512 of the central aspect of the left eye display 1502 are turned on and are shown in white, which may account for a large amount (e.g., 90 degrees of the horizontal field of view). Note that portions 1514 of the central aspect of the right eye display 1503 are turned on and are shown in white, which may account for a large amount (e.g., 90 degrees of the horizontal field of view). In FIG. 15B, a black dot 1516 is the focal point and is shown in both the left eye display 1518 and right eye display 1520. The orientation of the left eye 1522 and right eye 1524 are both angled inward, illustrating the process of the extra-ocular muscles moving the eyes inward when viewing an object in 3D space that is close by. Note that portions 1526 of the lateral side of the left eye display 1518 are turned off and are shown in black, which may account for a small amount (e.g., less than 10 degrees of the horizontal field of view). Note that portions 1528 of the lateral side of the right eye display 1520 are turned off and are shown in black, which may account for a small amount (e.g., less than 20 degrees of the horizontal field of view). Note that portions 1530 of the central and medial aspect of the left eye display 1518 are turned on and are shown in white, which may account for a large amount (e.g., 90 degrees of the horizontal field of view). Note that portions 1532 of the central aspect of the right eye display 1520 are turned on and are shown in white, which may account for a large amount (e.g., 90 degrees of the horizontal field of view). Thus, the portions of the field of view utilized can be altered in accordance with convergence. Thus, an example (but not limited to) of the convergence process is shown in this figure. First, from the left eye perspective: a) relative to looking straight ahead, occluding/eliminating the left portion of the display and associated voxels which would have been displayed with additional voxels displayed on the right portion of the display. Similarly, for the right eye occluding/eliminating the right portion of the display and adding additional voxels to the left portion. b) shifting the display of the convergence/focal point to the right for the left eye of the center point of the display proportional to the angular change based on distance of the view point from the convergence/focal point, similarly shifting the convergence/focal point to the left for the right eye; c) reducing the total voxels displayed for both eyes to reflect changes in the field of view when observing a close object.

Figure 16A:
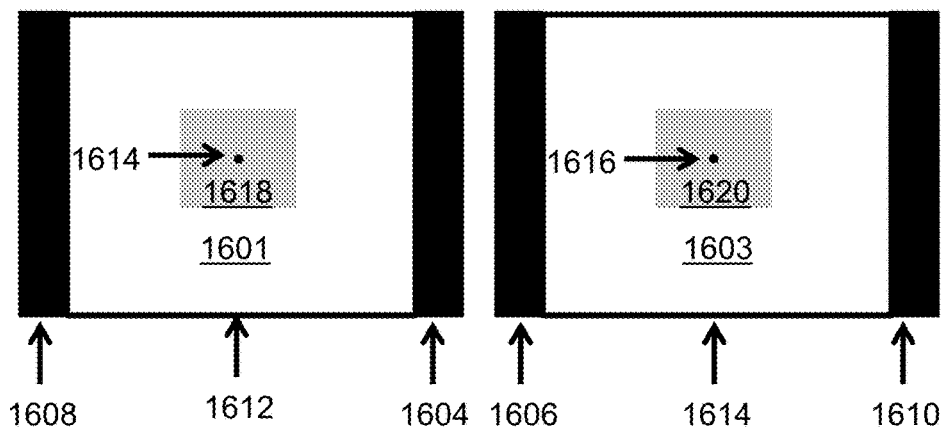
FIGS. 16A and 16B illustrate a process of providing increased resolution in the field of view corresponding to the fovea and is linked to the focal point.
Figure 16A:
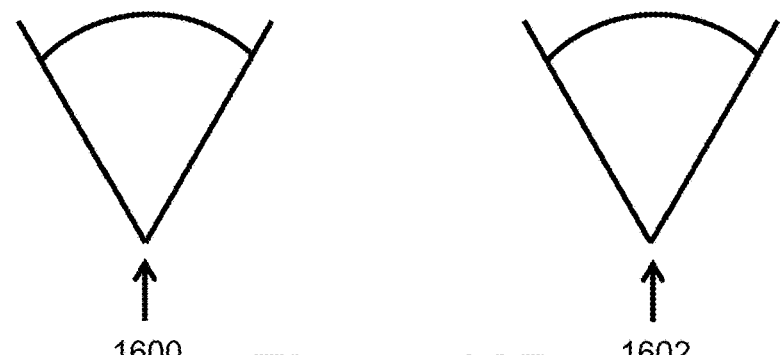
Figure 16B:
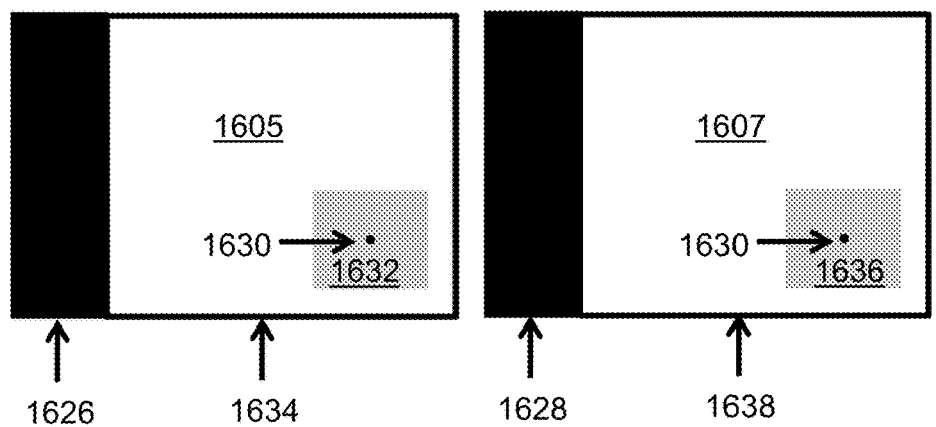
Figure 16B:
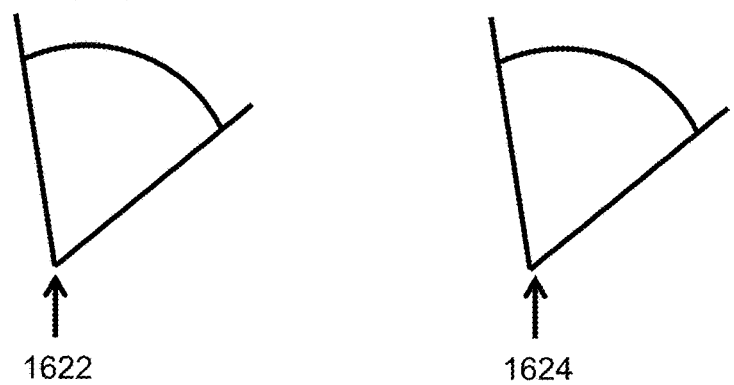

FIGS. 16A and 16B illustrate a process of providing increased resolution in the field of view corresponding to the fovea and is linked to the focal point. The human eye fovea is a small spot on the back of the eye with high visual acuity with an angular field of view of approximately 5 degrees. Away from the fovea, the visual acuity is not as sharp. Thus, a display which better utilizes this feature of the human fovea would have value. The visual acuity decreases at farther distances from the fovea in a non-linear fashion. Multiple types of HDUs could be utilized. In this example, the term pixels is used, but other types of HDUs could use this property. Specifically, the degrees of angular resolution in the field of view per pixel could likewise be variable. An example will be illustrated. Assume that there are 1000 pixels across the display in a horizontal fashion. Assume that the horizontal field of view is 80 degrees. If 250 pixels were allocated to the 5 degree high resolution band (based on the approximate field of view of the fovea), then each pixel in this region would subtend 0.02 degrees. The remaining 750 pixels would be allocated to the 75 degrees of lower resolution band, such that each pixel in this region would subtend 0.1 degrees. As the focal point pen moves to different regions in the display, the high-resolution band would change accordingly. In FIG. 16A, the left eye 1600 and right eye 1602 are oriented in a parallel fashion, which would be done when looking at an object at an infinite distance, such as the horizon. Note that portions 1604 of the medial side of the left eye display 1601 are turned off and are shown in black, which may account for a small amount (e.g., 5 degrees of the horizontal field of view). Note that portions 1606 of the medial side of the right eye display 1603 are turned off and are shown in black, which may account for a small amount (e.g., 5 degrees of the horizontal field of view). Note that portions 1608 of the lateral side of the left eye display 1601 are turned off and are shown in black, which may account for a small amount (e.g., 5 degrees of the horizontal field of view). Note that portions 1610 of the lateral side of the right eye display 1603 are turned off and are shown in black, which may account for a small amount (e.g., 5 degrees of the horizontal field of view). Note that a black dot is shown 1614 in the left eye display 1601, which corresponds to the horizontal center and vertical center of the left eye field of view. Note that a black dot is shown 1616 in the right eye display 1601, which corresponds to the horizontal center and vertical center of the right eye field of view. Note that a gray square 1618 shown within the left eye display 1601 corresponds to the high-resolution portion of the FOV (e.g., 0.02 degrees per pixel). The remainder of the left eye display 1601, which is turned on 1612 would have a lower resolution portion of the FOV (e.g., 0.1 degrees per pixel). Note that a gray square 1620 shown within the right eye display 1603 corresponds to the high-resolution portion of the FOV (e.g., 0.02 degrees per pixel). The remainder of the right eye display 1603, which is turned on 1614 would have a lower resolution portion of the FOV (e.g., 0.1 degrees per pixel). Thus, FIG. 16A illustrates Pixel display for one side of the HDU with a FOV of 80° and enhanced FOV of 5° given a disproportionate high number of pixels/angular FOV shown as the gray rectangle 1618 in the left eye display 1601 and the gray rectangle 1620 in the right eye display 1603. FIG. 16B illustrates the left eye 1622 and right eye 1624 both looking downward and to the right side. Note that portions 1626 of the lateral side of the left eye display 1605 are turned off and are shown in black, which may account for a small amount (e.g., 10 degrees of the horizontal field of view). Note that portions 1628 of the medial side of the right eye display 1607 are turned off and are shown in black, which may account for a small amount (e.g., 10 degrees of the horizontal field of view). Note that a black dot is shown in the left eye display 1605, which corresponds to the convergence point 1630. Note that a black dot is shown in the right eye display 1607, which corresponds to the convergence point 1630. Note that a gray square 1632 shown within the left eye display 1605 corresponds to the high-resolution portion of the FOV (e.g., 0.02 degrees per pixel). The remainder of the left eye display 1605, the portion which is turned on 1634, would have a lower resolution portion of the FOV (e.g., 0.1 degrees per pixel). Note that a gray square 1636 shown within the right eye display 1607 corresponds to the high-resolution portion of the FOV (e.g., 0.02 degrees per pixel). The remainder of the right eye display 1607, which is turned on 1638 would have a lower resolution portion of the FOV (e.g., 0.1 degrees per pixel). Thus, FIG. 16B illustrates a display wherein the angular field of view per area is variable. Thus, some regions in the display will be allocated higher number of pixels/angular FOV and some regions in the display will be allocated a lower number of pixels/angular FOV. An example wherein this may prove beneficial is during inspection of a close structure, such as a carotid artery for atherosclerotic plaques. The tip of the geo-registered focal point pen could be used to help the eyes track along a structure (e.g., carotid artery) to help the eyes follow along the structure and inspect for abnormalities. The geo-registered focal point pen would control the high resolution FOV and enhance overall detection.

FIGS. 17A and 17B illustrate a visual representation of convergence. In FIG. 17A, the volume of interest 1700 is shown. Note that left eye view point 1702 and right eye view point 1704 are shown. Note the left eye viewing angle 1706 and right eye viewing angle 1708 are shown. Note the convergence point 1712. Note that a center line is shown extending from a point on the plane between the eyes 1714 to (or near) the convergence point 1712. This line may help focus the user's attention. In FIG. 17B, the center line of one user could be displayed on all user's HDUs in a multi-HDU user situation. This would enable one user to see another user's center line. This could facilitate communication between multiple users. The center line 1710 would be placed in a fashion that would aid the user in their attention and their focus. For example, a center line 1720 appearing from overhead towards the object of interest (e.g., near the focal point 1718) may be the optimal placement. Note that the center line 1720 would only be visible to those wearing HDUs 1716 and would appear as a 3D structure in the left eye display 1722 and right eye display 1724.

Figure 18A:
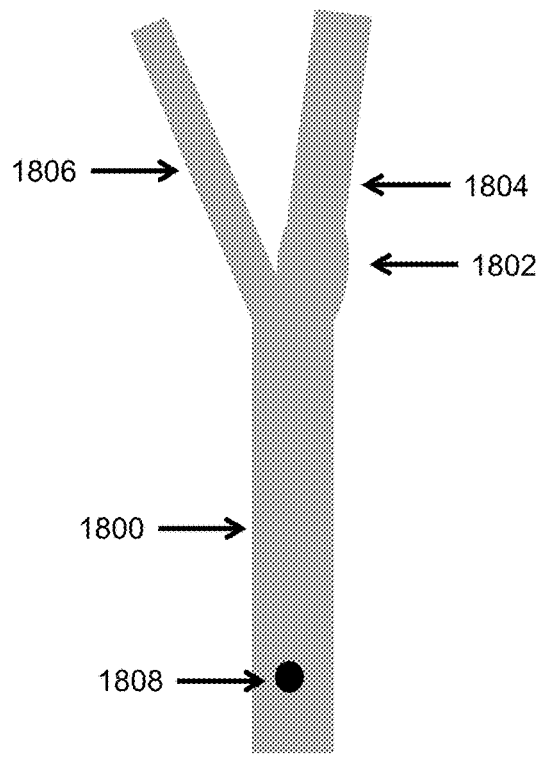
Figure 18B:
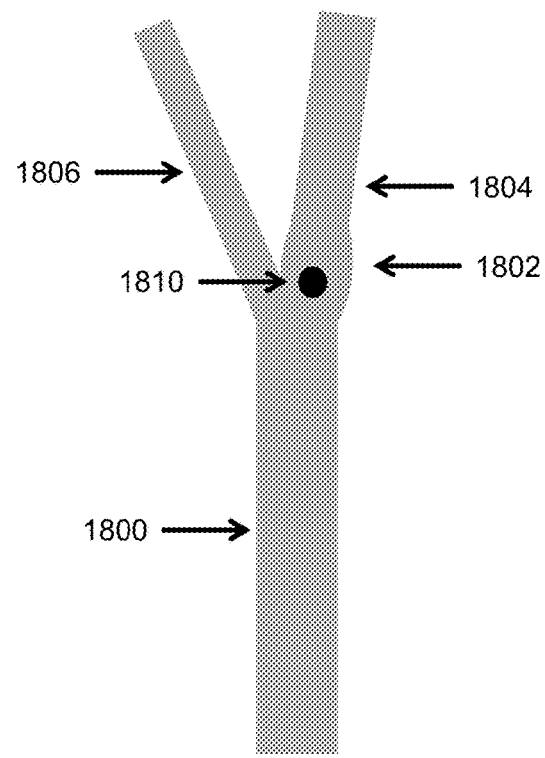
Figure 18C:
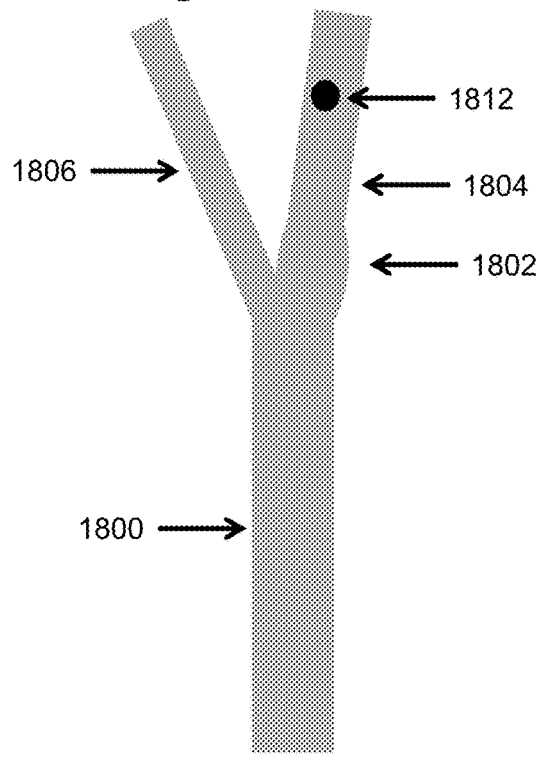
Figure 18D:
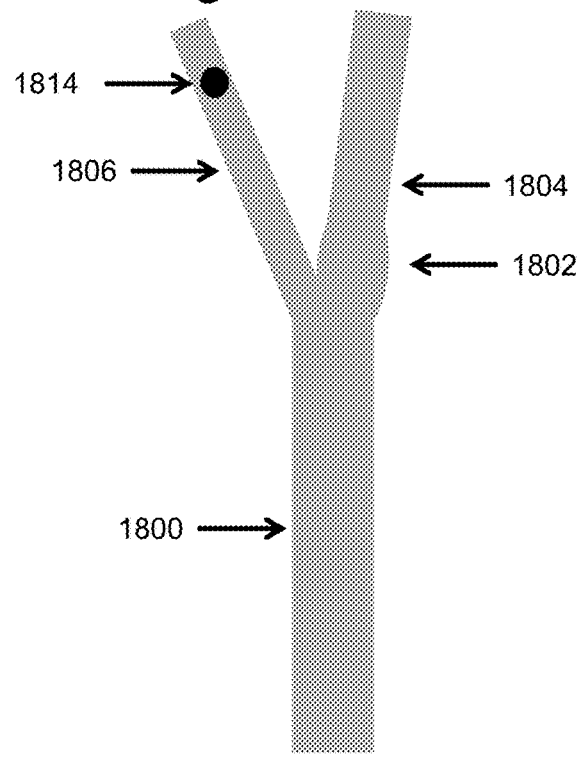

FIGS. 18A, 18B, 18C, and 18D illustrate methods of helping the radiologist in search pattern via utilization of saccades search technique. The example shown is a branching carotid artery arterial structure wherein the common carotid artery 1800, carotid bulb 1802, internal carotid artery 1804 and external carotid artery 1806 are shown. In FIG. 18A, a first black dot 1808 would appear at a first time point. The appearance of a first black dot 1808 (or other similar type object) would draw the eye in towards the new structure. This would force the human eye (and fovea region) to look in the region of the first black dot 1808 and examine those local structures, namely the common carotid artery 1800. In FIG. 18B, the first black dot 1808 disappears and a second black dot 1810 would appear at a second time point. The appearance of a second black dot 1810 (or other similar type object) would draw the eye in towards the new structure. This would force the human eye (and fovea region) to look in the carotid bulb 1802. In FIG. 18C, the second black dot 1810 disappears and a third black dot 1812 would appear at a third time point. The appearance of a third black dot 1812 (or other similar type object) would draw the eye in towards the new structure. This would force the human eye (and fovea region) to look in the internal carotid artery 1804. In FIG. 18D, the third black dot 1812 disappears and a fourth black dot 1814 would appear at a fourth time point. The appearance of a fourth black dot 1814 (or other similar type object) would draw the eye in towards the new structure. This would force the human eye (and fovea region) to look in the region of the external carotid artery 1806. Thus, utilization of planned structures that pop up on an image at strategic points would therefore use the human eye's natural ability to perform saccades and utilize the fovea. Segmentation algorithms could be utilized, and dots strategically positioned at sites where pathology is detected (e.g., by an AI algorithm) or where pathology is statistically most likely to occur (e.g., atherosclerosis in the carotid bulbs). Furthermore, the method that the radiologist could implement to help with the saccades includes on a set time (e.g., a new dot appears every 2 seconds) or could be by user control (e.g., user clicks a mouse and a new dot appears). Furthermore, the dots could be tied to a radiologist's checklist, such that when all dots are examined for a particular structure, evaluation of that structure would be complete. Furthermore, an eye tracking system could be utilized to help determine the optimum tools for lesion detection (e.g., whether it be saccades or smooth tracking, see FIG. 19, or combination thereof).

Figure 19A:
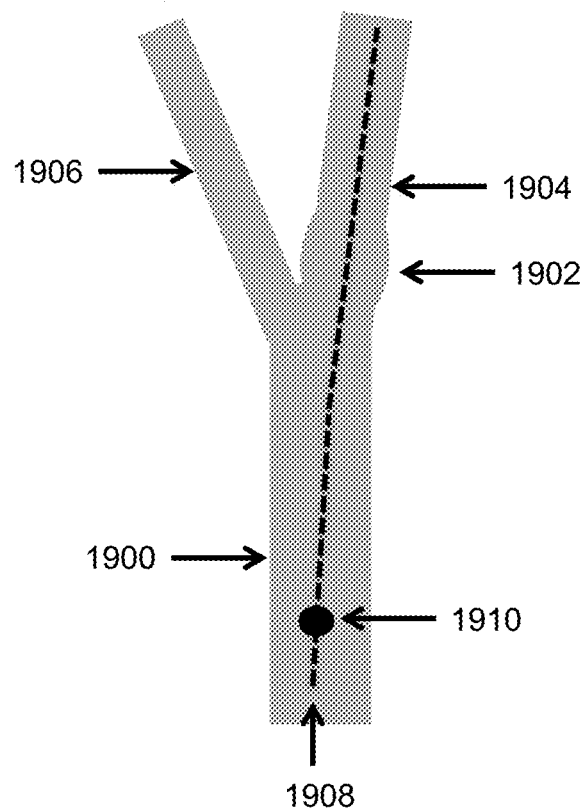
FIGS. 19A, 19B, 19C, and 19D illustrate a method of helping the radiologist in search pattern via utilization of smooth tracking search technique.
Figure 19B:
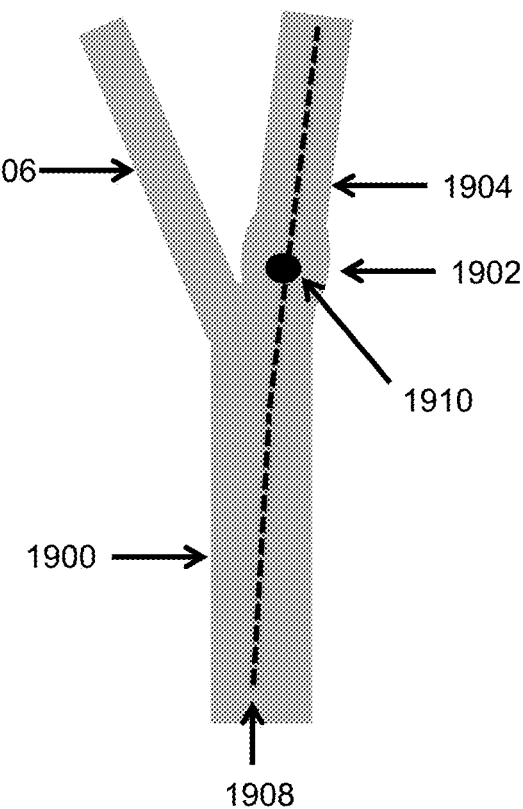
Figure 19C:
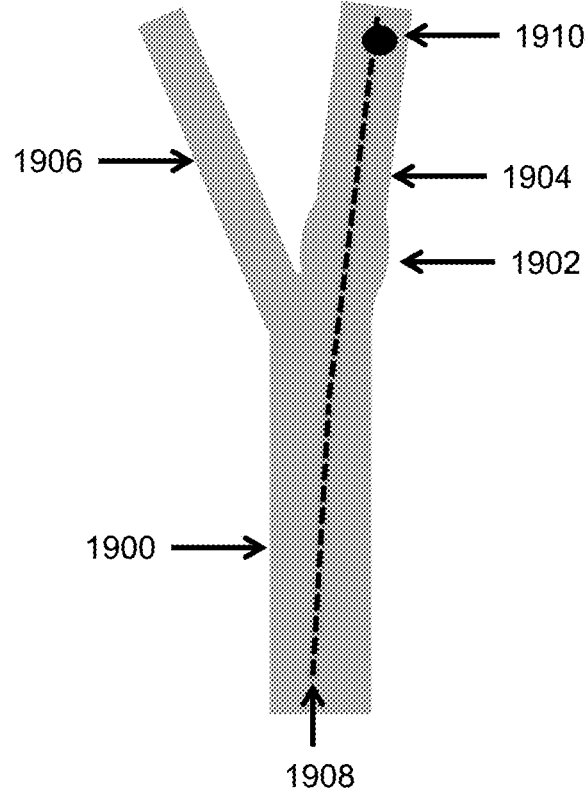
Figure 19D:
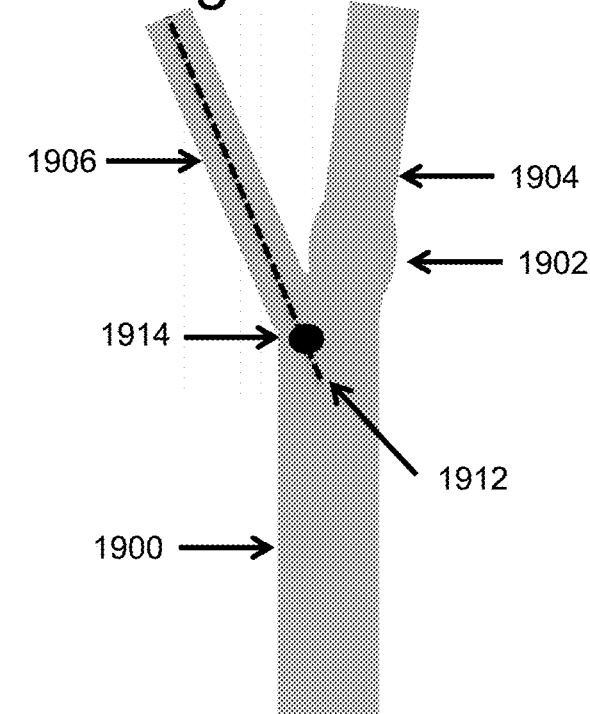

FIGS. 19A, 19B, 19C, and 19D illustrate a method of helping the radiologist in search pattern via utilization of smooth tracking search technique. The example shown is an arterial structure wherein the common carotid artery 1900, carotid bulb 1902, internal carotid artery 1904 and external carotid artery 1906 are shown. In FIG. 19A, a line 1908 is shown coursing from the common carotid artery 1900 through the carotid bulb 1902 and into the internal carotid artery 1904. The line 1908 would be an optional feature and would not be required for smooth tracking, and could be displayed or hidden by user preference. A black dot 1910 (or similar visual structure) is shown at the proximal portion of the common carotid artery 1900 at an initial time point. In FIG. 19B, the black dot 1910 is shown to be moving along that line and is now at the level of the carotid bulb 1902. Note that the black dot 1910 would be shown continuously and moved in a continuous fashion with a frame rate fast enough that the human eye sees smooth movement. In FIG. 19C, the black dot 1910 is shown to be moving along that line and is now at the level of the internal carotid artery 1904. Note that the black dot 1910 would be shown continuously and moved in a continuous fashion with a frame rate fast enough that the human eye sees smooth movement. After scanning the course of the common carotid artery 1900, carotid bulb 1902 and internal carotid artery 1904 for abnormalities, the radiologist may then elect to scan the external carotid artery 1906. A new line 1912 and a new black dot 1914 would then be used for scanning of the next structure. This new line 1912 and new black dot 1914 would suddenly appear at the new location and the human eye would perform a saccades movement to the new items. Then, the new black dot 1914 would smoothly move along the course of the external carotid artery 1906 in a continuous, smooth fashion with a frame rate fast enough that the human eye sees smooth movement. This would be analogous to a patient performing smooth tracking of a doctor's finger. Thus, a combination of saccades and smooth tracking eye movements can be utilized to help the radiologist improve visual tracking of abnormalities within structures. The rate of the smooth tracking and movement of the black dot would be controlled by the radiologist via adjusting input settings. Alternatively, this type of tracking could be linked to the movement of a focal point pen within the image. The human can move the black dot (via the focal point pen or GUI) or the computer or can control the black dot to aid the human in performing smooth tracking and assessment of the structure. Also, the radiologist can tab through various points of interest within the sub-volume as desired. This act will serve to mimic the human eyes' natural movement of performing saccades from one item of interest to another item of interest.

Figure 20A:
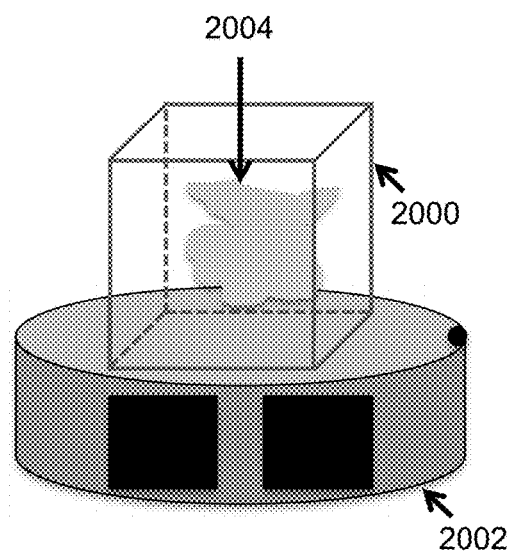
FIGS. 20A and 20B illustrate the capability of using the geo-registered platform to display a known pathology from a database next to another geo-registered platform with an unknown pathology from the patient's scan.
Figure 20B:
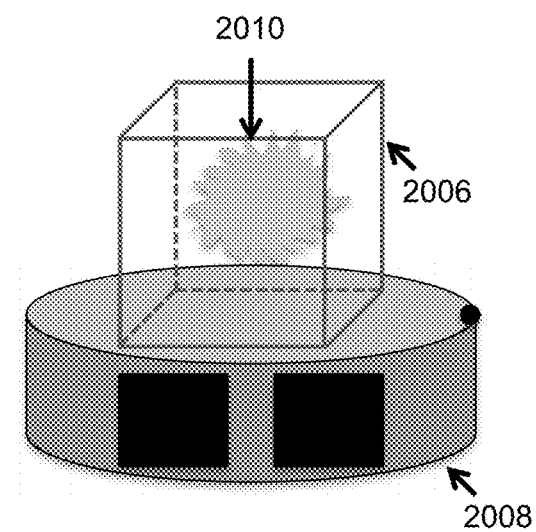

FIGS. 20A and 20B illustrate the capability of using the geo-registered platform to display a known pathology from a database next to another geo-registered platform with an unknown pathology from the patient's scan. In this figure, a first 3D cursor 2000 is shown affixed to a first geo-registered platform 2002. The first 3D cursor 2000 contains an unknown lesion 2004. For example, the unknown lesion 2004 could be a breast mass, but the precise diagnosis of the breast mass is not known. A second 3D cursor 2006 is shown affixed to a second geo-registered platform 2008. The second 3D cursor 2006 contains a known lesion 2010. For example, the known lesion 2010 could be a breast mass and the precise diagnosis of the breast mass is known to be an infiltrating ductal carcinoma. Note that the margins of the known mass 2010 in this example are spiculated whereas the margins of the unknown mass 2004 are lobulated. The radiologist would conclude from this comparison that the patient's pathology in the unknown lesion 2004 is different from the pathology in the known lesion 2010. Thus, the radiologist would have the ability to place the known pathology lesion 2010 on one pedestal. This can be imported from a known pathology database. The radiologist would have the ability to place unknown pathology lesion 2004 on another pedestal. This is from the patient's scan. These two could be compared in a side-by-side fashion.

Several features, aspects, embodiments, and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. An apparatus comprising:
a processor, which processes a 3D image dataset of a patient;
a head display unit (HDU) with both position tracking and orientation tracking on a geo-registration coordinate system;
a geo-registered tool with both position tracking and orientation tracking on the geo-registration coordinate system;
wherein the processor performs processing comprising:
registering the HDU and the geo-registered tool on the geo-registration coordinate system;
registering the 3D image dataset of the patient onto the geo-registered tool;
processing HDU data comprising position tracking and orientation tracking of the HDU on the geo-registration coordinate system;
processing geo-registered tool data comprising position tracking and orientation tracking of the geo-registered tool on the geo-registration coordinate system; and
displaying the 3D image dataset of the patient on the HDU.

2. The apparatus of claim 1 further comprising moving the geo-registered tool and a geo-registration device tracks location and orientation of the geo-registered tool and the processor causes the 3D image dataset of the patient to move with the geo-registered tool.

3. The apparatus of claim 1 wherein the geo-registered tool comprises a focal point pen.

4. The apparatus of claim 3 further comprising wherein the focal point pen designates a focal point in the 3D image dataset of the patient.

5. The apparatus of claim 3 further comprising wherein the focal point pen adds annotations to the 3D image dataset of the patient.

6. The apparatus of claim 3 further comprising wherein the focal point pen draws in the 3D image dataset of the patient.

7. The apparatus of claim 1 wherein the geo-registered tool comprises a mobile platform.

8. The apparatus of claim 7 further comprising wherein the platform moves a selected volume of the 3D image dataset of the patient independently from a non-selected volume of the 3D image dataset of the patient.

9. The apparatus of claim 1 wherein the geo-registered tool comprises a mobile multi-function tool.

10. The apparatus of claim 9 further comprising wherein the multi-function tool virtually grasps and manipulates selected tissue in the 3D image dataset of the patient.

11. The apparatus of claim 9 further comprising wherein the multi-function tool virtually ablates voxels from a tissue type of interest in the 3D image dataset of the patient.

12. The apparatus of claim 1 wherein the geo-registered tool comprises a mobile cutting tool.

13. The apparatus of claim 12 further comprising wherein the mobile cutting tool virtually cuts tissue in the 3D image dataset of the patient.

14. The apparatus of claim 1 wherein the geo-registered tools is a master control platform wherein the master control platforms performs at least one of the group comprising:
performing geo-registration of additional geo-registered tools;

changing the orientation of the 3D image dataset of the patient;
translating the 3D image dataset of the patient;
enlarging the size of 3D image dataset of the patient;
segmenting the 3D image dataset of the patient;
filtering the 3D image dataset of the patient;
selecting a portion of the 3D image dataset of the patient; and
zooming a selected portion of the 3D image dataset.

15. The apparatus of claim 14 wherein the master control platform works in conjunction with additional geo-registered tools to perform at least one of the group comprising:
changing the orientation of the 3D image dataset of the patient;
changing the position of the 3D image dataset of the patient;
changing the size of the 3D image dataset of the patient;
changing the interocular distance of a user;
segmenting the 3D image dataset of the patient;
filtering the 3D image dataset of the patient;
selecting a portion of 3D image dataset of the patient;
zooming in on a selected portion of the 3D image dataset of the patient;
zooming out from a selected portion of the 3D image dataset of the patient;
using a 3D cursor to perform image processing of a sub-volume of interest of the 3D image dataset of the patient;
calibrating a geo-registered tool with the 3D image dataset of the patient;
registering a geo-registered tool with a virtual tool;
performing convergence to a focal point within the 3D image dataset of the patient; and
altering the 3D image dataset of the patient.

16. The apparatus of claim 15 wherein altering of the 3D image dataset of the patient is performed by user inputted commands via at least one of a geo-registered tool, mouse, controller, joystick and the master control platform.

17. The apparatus of claim 15 wherein altering the 3D image dataset of the patient comprises at least one of the group comprising:
performing voxel manipulations of the 3D image dataset of the patient;
performing ablation of the 3D image dataset of the patient;
performing cutting of the 3D image dataset of the patient;
moving a selected portion of the 3D image dataset of the patient; and
moving cut portions of the 3D image dataset of the patient.

18. A method comprising:
registering a head display unit (HDU) and a geo-registered tool on a geo-registered coordinate system;
registering a 3D image of a patient onto the geo-registered tool;
tracking a position and orientation of the HDU on the geo-registered coordinate system;
tracking a position and orientation of the geo-registered tool on the geo-registered coordinate system; and
displaying the 3D image of the patient on the HDU.

19. The method of claim 18 further comprises moving the geo-registered tool wherein a geo-registration device tracks the location and orientation of the geo-registered tool and an image processor causes the 3D image of the patient to move with the geo-registered tool.

20. The method of claim 19 further comprising generating a virtual object to match the movements of the geo-registered tool wherein the virtual object is displayed on the HDU.

21. The method of claim 18 further comprising generating a focal point spot to assist a user perform a visual search through the 3D image.

22. The method of claim 21 further comprising wherein the focal point spot is controlled by at least one of the group comprising: movement of a geo-registered focal point pen; and, an artificial intelligence algorithm.

23. The method of claim 21 further comprising wherein the focal point spot appears and disappears at different spots within the 3D image of the patient to guide a saccadic movement of a user through the 3D image.

24. The method of claim 18 comprising displaying the virtual object in the three dimensional image with a head display unit and adjusting display of the three dimensional image responsive to movement of the head display unit 21 further comprising wherein the focal point spot moves continuously within the 3D image of the patient to guide a smooth tracking movement of a user through the 3D image of the patient.

25. The method of claim 18 further comprising viewing in a side-by-side fashion a first geo-registered platform affixed to a known pathology and a second geo-registered platform affixed to an unknown pathology to assist a user in the identification of the unknown pathology.

26. An apparatus comprising:
a processor, which processes a 3D image dataset of a patient;
a head display unit (HDU) with both position tracking and orientation tracking on a geo-registration coordinate system;
a geo-registered tool with both position tracking and orientation tracking on the geo-registration coordinate system;
wherein the processor performs processing comprising:
registering the HDU and the geo-registered tool on the geo-registration coordinate system;
registering the 3D image dataset of the patient onto the geo-registered tool;
processing HDU data comprising position tracking and orientation tracking of the HDU on the geo-registration coordinate system;
processing geo-registered tool data comprising position tracking and orientation tracking of the geo-registered tool on the geo-registration coordinate system; and
displaying the 3D image dataset of the patient on the HDU based on the position and orientation of the HDU and the position and orientation of the geo-registered tool.

27. The apparatus of claim 26 wherein the HDU adjusts the display based on where a user is looking.

28. The apparatus of claim 27 further comprising at least one of the group comprising:
the number of pixels on the medial portion of the field of view (FOV) is increased when a convergence point is moved from a position farther from the HDU to a position closer to the HDU;
the number of pixels on the lateral portion of the FOV is decreased when a convergence point is moved from a position farther from the HDU to a position closer to the HDU;

the number of pixels on the lateral portion of the FOV of the left eye display of the HDU is decreased when the user is looking to the right;

the number of pixels on the medial portion of the FOV of the left eye display of the HDU is increased when the user is looking to the right;

the number of pixels on the lateral portion of the FOV of the right eye display of the HDU is increased when the user is looking to the right;

the number of pixels on the medial portion of the FOV of the right eye display of the HDU is decreased when the user is looking to the right;

the number of pixels on the lateral portion of the FOV of the left eye display of the HDU is increased when the user is looking to the left;

the number of pixels on the medial portion of the FOV of the left eye display of the HDU is decreased when the user is looking to the left;

the number of pixels on the lateral portion of the FOV of the right eye display of the HDU is decreased when the user is looking to the left; and the number of pixels on the medial portion of the FOV of the right eye display of the HDU is increased when the user is looking to the left.

29. The apparatus of claim 27 further comprising wherein the display has a first portion with a first pixel resolution and a second portion with a second pixel resolution wherein the first pixel resolution is different from the second pixel resolution and wherein the first portion of the display is different from the second portion of the display.

30. The apparatus of claim 29 further comprising wherein the convergence point of where the user is looking is used to select the first portion of the display.

31. The apparatus of claim 26 comprising wherein the HDU adjusts the display based on the location of a convergence point.

32. The apparatus of claim 31 further comprising wherein the display has a first portion with a first pixel resolution and a second portion with a second pixel resolution wherein the first resolution is different from the second resolution and wherein the first portion of the display is different from the second portion of the display.

33. The apparatus of claim 32 further comprising wherein the convergence point determines the location of the first portion of the display.

34. The apparatus of claim 32 further comprising wherein the size of a structure determines the size of the first portion of the display.

35. A method comprising:

registering a head display unit (HDU) and a geo-registered tool on a geo-registration coordinate system;

affixing a 3D image dataset of a patient onto the geo-registered tool;

processing HDU data comprising position tracking and orientation tracking of the HDU on the geo-registration coordinate system;

processing geo-registered tool data comprising position tracking and orientation tracking of the geo-registered tool on the geo-registration coordinate system; and displaying the 3D image dataset of the patient on the HDU.

36. The method of claim 35 comprising adjusting display of the 3D image dataset of the patient on the HDU in accordance with a user's extra-ocular muscle movements.

37. The method of claim 36 further comprising wherein the display of the HDU has a first portion with a first pixel resolution and a second portion with a second pixel resolution wherein the first pixel resolution is different from the second pixel resolution and wherein the first portion of the display is different from the second portion of the display.

38. The method of claim 35 further comprising wherein a first digital object at a first location within the 3D image dataset of the patient is created to cause a user's eyes to perform a saccadic movement towards the first digital object at the first location within the 3D image dataset of the patient.

39. The method of claim 38 further comprising wherein the first digital object at the first location within the 3D image dataset disappears and a second digital object at a second location within the 3D image dataset appears wherein the second location within the 3D image dataset is different than the first location within the 3D image dataset and wherein the second digital object at the second location within the 3D image dataset causes the user's eyes to perform a saccadic movement towards the second digital object at the second location within the 3D image dataset to help the user perform a more comprehensive search.

40. The method of claim 39 further comprising wherein the user determines the timing of the disappearance of the first digital object at the first location within the 3D image dataset and the appearance of the second digital object at the second location within the 3D image dataset.

41. The method of claim 35 further comprising wherein a digital object is displayed within the 3D image dataset of the patient moving in a continuous fashion to cause a user's eyes to perform smooth tracking movements to help the user perform a more comprehensive search.

42. The method of claim 41 further comprising wherein the digital object is moved via at least one of the group comprising: user-directed movement of a focal point pen; a computer algorithm; and, user-directed input via a GUI.

43. The method of claim 42 further comprising wherein the user controls the rate of movement of the digital objects.

44. The method of claim 35 further comprising wherein digital objects are used in combination to cause the user to perform some saccadic movements and some smooth tracking movements to help the user perform a more comprehensive search.

* * * * *